United States Patent
Fukuzawa et al.

(10) Patent No.: US 9,250,142 B2
(45) Date of Patent: *Feb. 2, 2016

(54) PRESSURE SENSOR, MICROPHONE, BLOOD PRESSURE SENSOR, AND TOUCH PANEL

(71) Applicant: Kabushiki Kaisha Toshiba, Minato-ku (JP)

(72) Inventors: Hideaki Fukuzawa, Kanagawa-ken (JP); Yoshihiro Higashi, Kanagawa-ken (JP); Yoshihiko Fuji, Kanagawa-ken (JP); Michiko Hara, Kanagawa-ken (JP); Akio Hori, Kanagawa-ken (JP); Shiori Kaji, Kanagawa-ken (JP); Tomohiko Nagata, Kanagawa-ken (JP); Akiko Yuzawa, Kanagawa-ken (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 159 days.

This patent is subject to a terminal disclaimer.

(21) Appl. No.: 14/047,108

(22) Filed: Oct. 7, 2013

(65) Prior Publication Data

US 2014/0137668 A1  May 22, 2014

(30) Foreign Application Priority Data

Nov. 20, 2012  (JP) .................................. 2012-254784

(51) Int. Cl.
| | |
|---|---|
| *G01L 1/12* | (2006.01) |
| *A61B 5/021* | (2006.01) |
| *H04R 19/04* | (2006.01) |
| *B81B 3/00* | (2006.01) |
| *G01L 3/10* | (2006.01) |

(52) U.S. Cl.
CPC ................. *G01L 1/125* (2013.01); *A61B 5/021* (2013.01); *B81B 3/0086* (2013.01); *H04R 19/04* (2013.01); *A61B 2562/0247* (2013.01); *B81B 2201/0257* (2013.01); *G01L 3/102* (2013.01)

(58) Field of Classification Search
CPC ........... G01L 9/16; G01L 1/125; G01L 3/102; G01R 33/09; G11B 5/3146; H04R 19/04; G01D 5/2013
USPC .......... 73/760, 779, 862.69, 862.331–862.335
See application file for complete search history.

(56) References Cited

U.S. PATENT DOCUMENTS

| | | | |
|---|---|---|---|
| 8,973,446 B2* | 3/2015 | Fukuzawa et al. ............... 73/779 |
| 2004/0079174 A1* | 4/2004 | Horiuchi ................... 73/862.338 |

(Continued)

FOREIGN PATENT DOCUMENTS

JP  2007-180201  7/2007

*Primary Examiner* — Max Noori
(74) *Attorney, Agent, or Firm* — Oblon, McClelland, Maier & Neustadt, L.L.P.

(57) ABSTRACT

According to one embodiment, a pressure sensor includes a base unit, a film unit, and a plurality of sensing elements. The plurality of sensing elements is provided on the film unit radially with respect to a centroid of the film unit. The plurality of sensing elements has a first side and a second side intersecting the first side. Each of the plurality of sensing elements includes a first magnetic layer, a second magnetic layer, and an intermediate layer. Each of the plurality of sensing elements has a shape anisotropy characterized by a length of the first side being longer than a length of the second side intersecting the first side. The plurality of sensing elements is provided at lines having radial configurations extending from the centroid to have a prescribed angle between the first side and the line.

20 Claims, 21 Drawing Sheets

(56) References Cited

U.S. PATENT DOCUMENTS

| | | |
|---|---|---|
| 2011/0295128 A1 | 12/2011 | Yuasa et al. |
| 2012/0079887 A1 | 4/2012 | Giddings et al. |
| 2012/0245477 A1 | 9/2012 | Giddings et al. |
| 2013/0170669 A1 | 7/2013 | Fukuzawa et al. |
| 2013/0229895 A1* | 9/2013 | Shiroishi et al. ........... 369/13.14 |
| 2013/0255069 A1* | 10/2013 | Higashi et al. ................. 29/595 |

* cited by examiner

US 9,250,142 B2

PRESSURE SENSOR, MICROPHONE, BLOOD PRESSURE SENSOR, AND TOUCH PANEL

CROSS-REFERENCE TO RELATED APPLICATIONS

This application is based upon and claims the benefit of priority from Japanese Patent Application No. 2012-254784, filed on Nov. 20, 2012; the entire contents of which are incorporated herein by reference.

FIELD

Embodiments described herein relate generally to a pressure sensor, microphone, blood pressure sensor, and touch panel.

BACKGROUND

In a capacitive pressure sensor that converts sound into an electrical signal according to a capacitance change, the entire diaphragm is used as a portion of the electrode. Therefore, in the case where the pressure sensor is downsized, both the diaphragm and the surface area of the electrode are smaller; and there is a risk that the sensitivity may degrade.

BRIEF DESCRIPTION OF THE DRAWINGS

FIG. 4 is a schematic view showing effects of the sensing elements 50, 150, and 150a;

DETAILED DESCRIPTION

Figure 1:
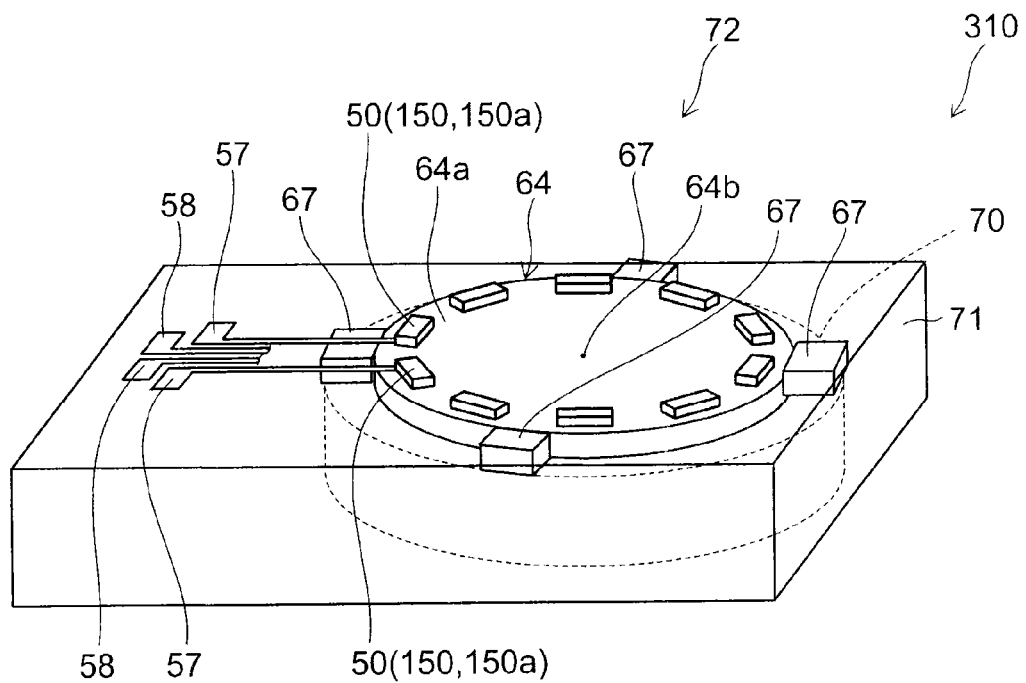
FIG. 1 is a schematic perspective view showing a pressure sensor 310 according to a first embodiment.

In general, according to one embodiment, a pressure sensor includes a base unit, a film unit, and a plurality of sensing elements. The film unit is provided in the base unit. The film unit is flexible. The plurality of sensing elements is provided on the film unit radially with respect to a centroid of the film unit. The plurality of sensing elements has a first side and a second side intersecting the first side. Each of the plurality of sensing elements includes a first magnetic layer, a second magnetic layer provided on the film unit, and an intermediate layer provided between the first magnetic layer and the second magnetic layer. The first magnetic layer and the second magnetic layer free magnetic layers. Each of the plurality of sensing elements has a shape anisotropy characterized by a length of the first side being longer than a length of the second side. The plurality of sensing elements is provided at lines having radial configurations extending from the centroid to have a prescribed angle between the first side and the line.

Embodiments will now be described with reference to the drawings.

The drawings are schematic or conceptual; and the proportions of sizes between portions, etc., are not necessarily the same as the actual values thereof. Further, the dimensions and/or the proportions may be illustrated differently between the drawings, even for identical portions.

In the drawings and the specification of the application, components similar to those described in regard to a drawing thereinabove are marked with like reference numerals, and a detailed description is omitted as appropriate.

First Embodiment

FIG. 1 is a schematic perspective view showing a pressure sensor 310 according to a first embodiment.

In FIG. 1, the insulating portions are not shown, and mainly the conductive portions are shown for easier viewing of the drawing. A portion of multiple sensing elements 50 are shown for easier viewing of the drawing.

As shown in FIG. 1, a sensor unit 72 and a base unit 71 are provided in the pressure sensor 310.

The sensor unit 72 is provided on the base unit 71.

The sensor unit 72 includes a film unit 64, a fixing unit 67, and the sensing elements 50.

The film unit 64 is a film that is flexible. The film unit 64 is flexible with respect to a direction perpendicular to a film surface 64a. When an external pressure is applied, the film unit 64 deflects to cause strain to occur in the sensing elements 50 provided on the film unit 64. The external pressure may be pressure due to, for example, a sound wave, an ultrasonic wave, being pressed, etc. As described below, the pressure sensor 310 may be used in, for example, a microphone, a blood pressure sensor, a touch panel, etc.

There are cases where the film unit 64 is formed continuously outside the portion that deflects due to the external pressure. In the specification, the section that is used as the film unit 64 has a constant film thickness, is thinner than the fixing ends, and deflects due to the external pressure.

The film unit 64 may be formed of, for example, an insulating material. The film unit 64 may include, for example, silicon oxide, silicon nitride, etc. The film unit 64 may be formed of a semiconductor material such as silicon, etc. The film unit 64 may be formed of, for example, a metal material, etc.

The thickness dimension of the film unit 64 may be, for example, not less than 200 nm and not more than 3 µm. In such a case, it is favorable to be not less than 300 nm and not more than 1.5 µm.

In the case where the planar configuration of the film unit 64 is a circle as shown in FIG. 1, the diametrical dimension of the film unit 64 may be, for example, not less than 1 µm and not more than 600 µm. In such a case, it is favorable to be not less than 60 µm and not more than 600 µm.

The fixing unit 67 fixes the film unit 64 to the base unit 71. The thickness dimension of the fixing unit 67 is thicker than that of the film unit 64 so as not to deflect even when the external pressure is applied.

For example, the fixing unit 67 may be provided at uniform spacing at the circumferential edge of the film unit 64.

Despite having a segmented structure in FIG. 1, the fixing unit 67 may be provided to continuously enclose the entire periphery of the film unit 64. For example, as shown in FIG. 11D described below, the periphery of the film unit 64 may be a continuous fixing end.

The fixing unit 67 may be formed from, for example, the same material as the material of the base unit 71. In such a case, the fixing unit 67 may be formed from, for example, silicon, etc.

It is also possible to form the fixing unit 67 from, for example, the same material as the material of the film unit 64.

The sensing elements 50 are multiply provided on the film surface 64a of the film unit 64.

The details relating to the configuration and disposition of the sensing elements 50 are described below.

Interconnects 57 are electrically connected to first magnetic layers 10 of the multiple sensing elements 50, respectively. Interconnects 58 are electrically connected to second magnetic layers 20 of the multiple sensing elements 50, respectively. The interconnect 58 and the interconnect 57 may be respectively connected electrically via a first electrode 51 and a second electrode 52 described below.

The interconnects 57 and the interconnects 58 extend outward from the film unit 64 through the interior of the fixing unit 67 or on the fixing unit 67.

In such a case, the orientation of the current caused to flow in the sensing element 50 may be the direction from the first magnetic layer 10 toward the second magnetic layer 20 or the direction from the second magnetic layer 20 toward the first magnetic layer 10.

The base unit 71 has a plate configuration and a hollow portion 70 in the interior of the base unit 71.

The base unit 71 may be formed of an insulating material or a semiconductor such as silicon, etc. The film unit 64 may include, for example, silicon oxide, silicon nitride, etc. Or, a metal material or a semiconductor material such as silicon, etc., may be used.

The interior of the hollow portion 70 may be in a vacuum state (a low-pressure state lower than 1 atmosphere) or may be filled with a liquid or a gas such as air, an inert gas, etc. In other words, it is sufficient for the interior of the hollow portion 70 to allow the film unit 64 to deflect.

The film unit 64 is provided above the hollow portion 70; and the film unit 64 is fixed to the base unit 71 by the fixing unit 67.

The configuration of the sensing element 50 will now be described further.

Figure 2:
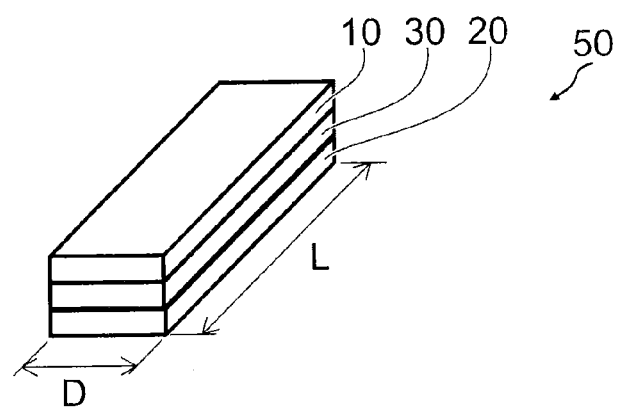
FIG. 2 is a schematic perspective view showing the configuration of the sensing element 50.

FIG. 2 is a schematic perspective view showing the configuration of the sensing element 50.

As shown in FIG. 2, the sensing element 50 includes, for example, the first magnetic layer 10, the second magnetic layer 20 provided on the film unit 64, and an intermediate layer 30 provided between the first magnetic layer 10 and the second magnetic layer 20.

The first magnetic layer 10 and the second magnetic layer 20 are free magnetic layers.

The thickness dimensions of the first magnetic layer 10 and the second magnetic layer 20 may be, for example, not less than 1 nm and not more than 20 nm. In such a case, it is favorable for the thickness dimensions of the first magnetic layer 10 and the second magnetic layer 20 to be not less than 2 nm and not more than 6 nm.

The first magnetic layer 10 and the second magnetic layer 20 are formed from a material having a large absolute value of the magnetostriction constant. In such a case, the absolute value of the magnetostriction constant can be changed by the type of the material, the added elements, etc. Also, it is possible to greatly change the magnetostriction by not only the magnetic material itself but also by the material and configuration of a nonmagnetic layer formed adjacently to the magnetic layer. The absolute value of the magnetostriction constant may be greater than, for example, $10^{-6}$. In such a case, it is favorable for the absolute value of the magnetostriction constant to be greater than, for example, $10^{-5}$.

By setting the absolute value of the magnetostriction constant to be large, the change amount of the magnetization direction corresponding to the change of the stress can be increased.

The first magnetic layer 10 and the second magnetic layer 20 may include a material having a magnetostriction constant having a positive sign or a material having a magnetostriction constant having a negative sign. The absolute value of the magnetostriction constant of the first magnetic layer 10 may be different from the absolute value of the magnetostriction constant of the second magnetic layer 20.

The materials of the first magnetic layer 10 and the second magnetic layer 20 may be, for example, at least one selected from Fe, Co, and Ni or an alloy including the at least one selected from Fe, Co, and Ni. An added element may be added to these materials.

It is also possible to add B, Al, Si, Mg, C, Ti, V, Cr, Mn, Cu, Zn, Ga, Zr, Hf, etc., to such metals and alloys as an added element or an extremely thin layer.

It is possible to use not only a crystal magnetic layer but also an amorphous magnetic layer.

It is also possible to use a magnetic layer of an oxide or nitride.

The materials of the first magnetic layer 10 and the second magnetic layer 20 may be, for example, an FeCo alloy, a NiFe alloy, etc. Or, the materials of the first magnetic layer 10 and the second magnetic layer 20 may be, for example, an Fe—Co—Si alloy, an Fe—Co—Si—B alloy. Another examples is a Tb-M-Fe alloy (M being Sm, Eu, Gd, Dy, Ho, or Er) for which λs>100 ppm, a Tb-M1-Fe-M2 alloy (M1 being Sm, Eu, Gd, Dy, Ho, or Er and M2 being Ti, Cr, Mn, Co, Cu, Nb, Mo, W, or Ta), an Fe-M3-M4-B alloy (M3 being Ti, Cr, Mn, Co, Cu, Nb, Mo, W, or Ta and M4 being Ce, Pr, Nd, Sm, Tb, Dy, or Er), Ni, Al—Fe, ferrite ($Fe_3O_4$, $(FeCo)_3O_4$, etc.), and the like.

The first magnetic layer 10 and the second magnetic layer 20 may have two-layer structures.

For example, the first magnetic layer 10 and the second magnetic layer 20 may include a layer including FeCo (e.g., a layer of CoFe or a layer of an alloy including CoFe) and the following layers stacked with the layer including FeCo.

The layer that is stacked with the layer including FeCo may be formed from an Fe—Co—Si—B alloy, a Tb-M-Fe alloy (M being Sm, Eu, Gd, Dy, Ho, or Er) for which λs>100 ppm, a Tb-M1-Fe-M2 alloy (M1 being Sm, Eu, Gd, Dy, Ho, or Er and M2 being Ti, Cr, Mn, Co, Cu, Nb, Mo, W, or Ta), an Fe-M3-M4-B alloy (M3 being Ti, Cr, Mn, Co, Cu, Nb, Mo, W, or Ta and M4 being Ce, Pr, Nd, Sm, Tb, Dy, or Er), Ni, Al—Fe, ferrite ($Fe_3O_4$, $(FeCo)_3O_4$, etc.), and the like.

The intermediate layer 30 may be a nonmagnetic layer.

The intermediate layer 30 may be formed of, for example, a metal material, an insulating material, etc.

Examples of the metal material include, for example, Cu, Au, Ag, etc. In the case where the intermediate layer 30 is formed from the metal material, the thickness dimension of the intermediate layer 30 may be, for example, not less than 1 nm and not more than 7 nm.

Examples of the insulating material include, for example, magnesium oxide (MgO, etc.), aluminum oxide ($Al_2O_3$, etc.), titanium oxide (TiO, etc.), zinc oxide (ZnO, etc.), and the like. In the case where the intermediate layer 30 is formed from the insulating material, the thickness dimension of the intermediate layer 30 may be, for example, not less than 1 nm and not more than 3 nm.

In the case of the intermediate layer 30 formed of the metal material, a giant magnetoresistance effect (GMR) occurs.

In the case of the intermediate layer 30 formed of the insulating material, a tunneling magnetoresistance effect (TMR) occurs.

CPP-GMR (Current-Perpendicular-to-Plane Giant Magnetoresistance) that causes a current to flow along the stacking direction of the sensing element 50 is used in the pressure sensor 310.

The intermediate layer 30 may have a CCP (Current-Confined-Path) structure in which multiple metal current paths are provided to pierce the insulating layer in the film thickness direction. In such a case, the metal current paths may have a width dimension or a diameter dimension not less than about 1 nm and not more than about 5 nm. In such a case as well, CPP-GMR is used in the pressure sensor 310.

Here, there are cases where the first magnetic layer 10, which is on the intermediate layer 30 that includes an oxide such as magnesium oxide, is formed from a material having a positive magnetostriction constant. For example, there are cases where stacked layers of a layer made of CoFeB, a layer made of CoFe, and a layer made of NiFe are used as the first magnetic layer 10. In such a case, in the case where the proportion of nickel in the layer made of NiFe of the uppermost layer is increased, the magnetostriction constant of the layer made of NiFe becomes negative; and the absolute value of the magnetostriction constant also increases. In the case where the magnetostriction constant becomes negative, there is a risk that the positive magnetostriction on the intermediate layer 30 may be canceled. Therefore, it is favorable for the proportion of nickel in the layer made of NiFe of the uppermost layer to be lower than the proportion of nickel in a layer made of $Ni_{81}Fe_{19}$ which is generally used. For example, it is favorable for the proportion of nickel in the layer made of NiFe of the uppermost layer to be less than 80 atomic percent (atomic %).

Figure 3A:
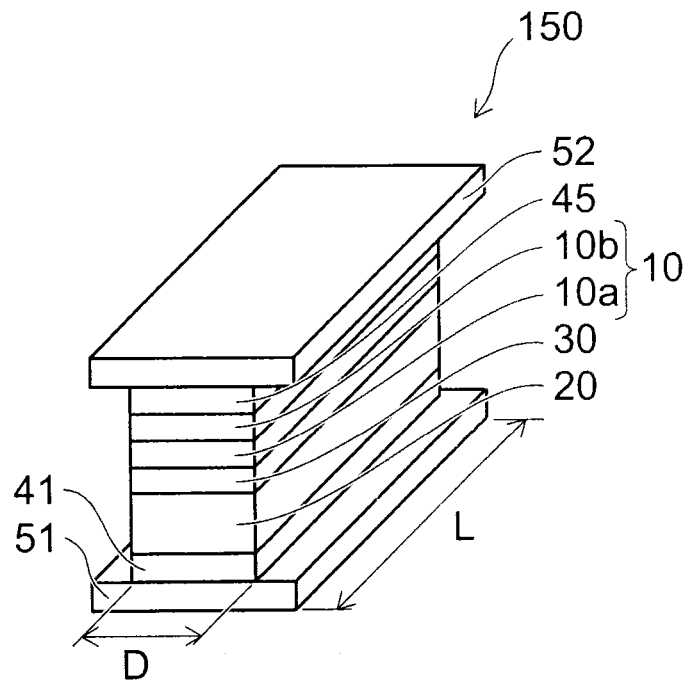
FIGS. 3A and 3B are schematic perspective views showing configurations of sensing elements 150 and 150a according to other embodiments.
Figure 3B:
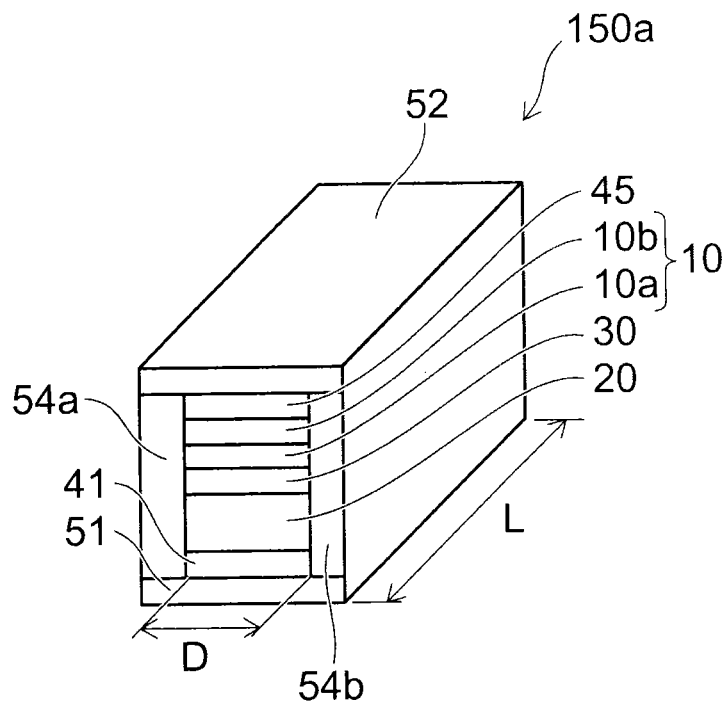

FIGS. 3A and 3B are schematic perspective views showing configurations of sensing elements 150 and 150a according to other embodiments.

As shown in FIGS. 3A and 3B, the sensing element 150 may include, for example, the first electrode 51, a buffer layer 41, the second magnetic layer 20, the intermediate layer 30, the first magnetic layer 10, a cap layer 45, and the second electrode 52 stacked in this order.

The first electrode 51 and the second electrode 52 may be formed from a nonmagnetic body that is conductive. In such a case, the first electrode 51 and the second electrode 52 may be formed from, for example, Au, Cu, Ta, Al, etc.

The first electrode 51 and the second electrode 52 may be formed from a soft magnetic body that is conductive. If the first electrode 51 and the second electrode 52 are formed from a soft magnetic body, the magnetic noise from the outside can be reduced. In such a case, the first electrode 51 and the second electrode 52 may be formed from, for example, permalloy (NiFe alloy), silicon steel (FeSi alloy), etc.

The buffer layer 41 may be, for example, an amorphous layer including Ta and Ti. The thickness dimension of the buffer layer 41 may be, for example, not less than 1 nm and not more than 10 nm. The buffer layer 41 also may be used as a seed layer for promoting the crystal orientation. In the case where the buffer layer 41 is a seed layer for promoting the crystal orientation, the buffer layer 41 may be a layer formed from Ru, NiFe, etc. Also, layers formed from Ru, NiFe, etc., may be stacked.

The second magnetic layer 20 and the intermediate layer 30 may be similar to those described above.

The first magnetic layer 10 has the two-layer structure described above. The first magnetic layer 10 includes a magnetic stacked film 10a and a highly magnetostrictive film 10b.

The magnetic stacked film 10a is provided to increase the change rate of the magnetoresistance described below. The magnetic stacked film 10a may be formed from, for example, the layer including cobalt, iron, nickel, etc., described above. For example, a CoFeB layer, etc., may be used. The thickness dimension of the magnetic stacked film 10a may be, for example, not less than 1 nm and not more than 3 nm.

The highly magnetostrictive film 10b is provided between the magnetic stacked film 10a and the cap layer 45. The highly magnetostrictive film 10b may be formed from, for example, the Fe—Co—Si—B alloy, etc., described above. The thickness dimension of the highly magnetostrictive film 10b may be, for example, not less than 1 nm and not more than 5 nm.

The cap layer 45 is provided between the highly magnetostrictive film 10b and the second electrode 52. The thickness dimension of the cap layer 45 may be, for example, not less than 1 nm and not more than 5 nm.

As shown in FIG. 3B, an insulating layer 54a and an insulating layer 54b may be provided at the side walls of the stacked body made of the buffer layer 41, the second magnetic layer 20, the intermediate layer 30, the first magnetic layer 10, and the cap layer 45.

The insulating layer 54a and the insulating layer 54b may be formed from, for example, aluminum oxide (e.g., $Al_2O_3$), silicon oxide (e.g., $SiO_2$), etc.

The thickness dimensions of the insulating layer 54a and the insulating layer 54b may be, for example, not less than 1 nm and not more than 5 nm.

By providing the insulating layer 54a and the insulating layer 54b, leak current flowing at the periphery can be suppressed.

It is sufficient for the sensing elements 50, 150, and 150a to be extremely small.

Therefore, the surface area of the sensing elements 50, 150, and 150a can be sufficiently less than the surface area of the film unit 64 that deflects due to the pressure. For example, the surface area of the sensing elements 50, 150, and 150a can be ⅕ of the surface area of the film unit 64 or less.

For example, in the case where the diametrical dimension of the film unit 64 is about 60 µm, a length D of the short side (corresponding to an example of the second side) of the sensing elements 50, 150, and 150a may be 12 µm or less. For example, in the case where the diametrical dimension of the film unit 64 is about 600 µm, the length D of the short side of the sensing elements 50, 150, and 150a may be 120 µm or less.

In such a case, it is unnecessary for the sensing elements 50, 150, and 150a to be excessively small considering the patterning precision, etc., of the sensing elements 50, 150, and 150a. Therefore, the length D of the short side of the sensing elements 50, 150, and 150a may be, for example, not less than 0.1 µm and not more than 30 µm. It is favorable for a length L of the long side (corresponding to an example of the first side) to be within, for example, a range not less than 0.2 µm and not more than 60 µm.

As shown in FIG. 2 and FIGS. 3A and 3B, the planar configurations of the sensing elements 50, 150, and 150a are rectangles. Therefore, the dimension L of the long side is greater than the dimension D of the short side. Although the proportion of the dimension L of the long side and the dimension D of the short side is not particularly limited, for example, the dimension L of the long side may be 2 times the dimension D of the short side or more. The planar configurations of the sensing elements 50, 150, and 150a are not limited to rectangles; and it is sufficient for the dimension L of one side to be larger than the dimension D of a side intersecting the one side. For example, the planar configurations of the sensing elements 50, 150, and 150a may be quadrilaterals such as parallelograms, etc.

In the configuration in which the dimension L of the one side is larger than the dimension D of the side intersecting the one side, the magnetization direction is the direction along the side having the dimension L due to the shape magnetic anisotropy.

Thus, by utilizing the shape anisotropy, it is possible to set the magnetization direction of the sensing element to be in any direction in the state in which the external pressure is zero without using magnetization direction control such as the hard bias of CoPt and the like, the exchange coupling bias of IrMn and the like, etc. In such a case, it is also possible to use a hard bias and/or an exchange coupling bias if the magnetization direction is a constant direction in the film plane. However, in the case where the initial magnetization directions of multiple sensing elements are set to be oriented in different directions in the film plane as in the embodiment, bias control by a hard bias or exchange coupling bias is not actually feasible. By utilizing the shape anisotropy in the embodiment, it is possible to set the initial magnetization direction for each of the multiple sensing elements 50 provided in the film unit 64 to be utilized effectively in the device operation. This is elaborated below.

Effects of the sensing elements 50, 150, and 150a will now be described.

Figure 4:
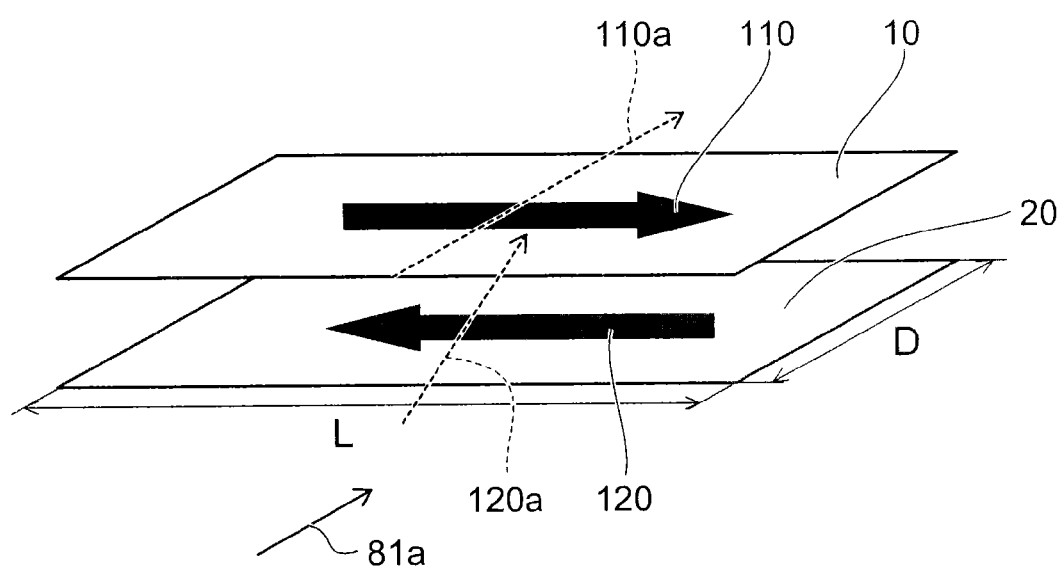

FIG. 4 is a schematic view showing effects of the sensing elements 50, 150, and 150a.

In FIG. 4, only the first magnetic layer 10 and the second magnetic layer 20 are shown for easier viewing of the drawing.

As shown in FIG. 4, magnetization directions 110 and 120 are directions along the long sides of the sensing elements 50, 150, and 150a due to the shape magnetic anisotropy described above. In such a case, the magnetization direction 110 of the first magnetic layer 10 is different from the magnetization direction 120 of the second magnetic layer 20 due to the effect of the demagnetizing field. For example, as shown in FIG. 4, the magnetization direction 110 and the magnetization direction 120 are reversely oriented.

When the film unit 64 deflects due to the external pressure, stress 81 is applied to the first magnetic layer 10 and the second magnetic layer 20.

Then, the magnetization direction 110 of the first magnetic layer 10 and the magnetization direction 120 of the second magnetic layer 20 change according to the stress 81 that is applied due to an inverse-magnetostriction effect.

In the inverse-magnetostriction effect, the easy magnetization axis changes due to the sign (positive or negative) of the magnetostriction constant. In other words, the magnetization directions 110 and 120 change according to the stress 81 that is applied.

For example, in the case where the magnetostriction constant has a positive sign, a direction 81a of the stress 81 is the easy magnetization axis. Therefore, in the case where the magnetostriction constant has a positive sign, the magnetization directions 110 and 120 rotate toward the direction of the easy magnetization axis, i.e., the direction 81a of the stress 81, as shown in FIG. 4. Conversely, in the case where the magnetostriction constant has a negative sign, a direction perpendicular to the direction 81a of the stress 81 is the easy magnetization axis. Therefore, in the case where the magnetostriction constant has a negative sign, the magnetization directions 110 and 120 rotate toward the direction that is perpendicular to the direction 81a of the stress 81.

That is, the disposition directions of the sensing elements 50, 150, and 150a are determined by the magnetization directions 110 and 120 and the sign of the magnetostriction constant.

The absolute value of the magnetostriction constant of the first magnetic layer 10 is set to be different from the absolute value of the magnetostriction constant of the second magnetic layer 20. Therefore, an angular difference occurs between a magnetization direction 110a and a magnetization direction 120a after the rotation.

The electrical resistance changes according to the angular difference between the magnetization direction 110a and the magnetization direction 120a due to the magnetoresistance effect.

Therefore, not only the stress that is applied but also the external pressure can be determined by causing a current to flow in the sensing elements 50, 150, and 150a and measuring the electrical resistance.

ΔR/R is called the MR ratio, where R is the resistance of the low resistance state, and ΔR is the change amount of the electrical resistance that changes due to the magnetoresistance effect.

The dispositions of the sensing elements 50, 150, and 150a will now be described further.

Here, although the disposition of the sensing elements 50 are shown as an example, the dispositions of the sensing elements 150 and 150a may be similar.

Figure 5A:
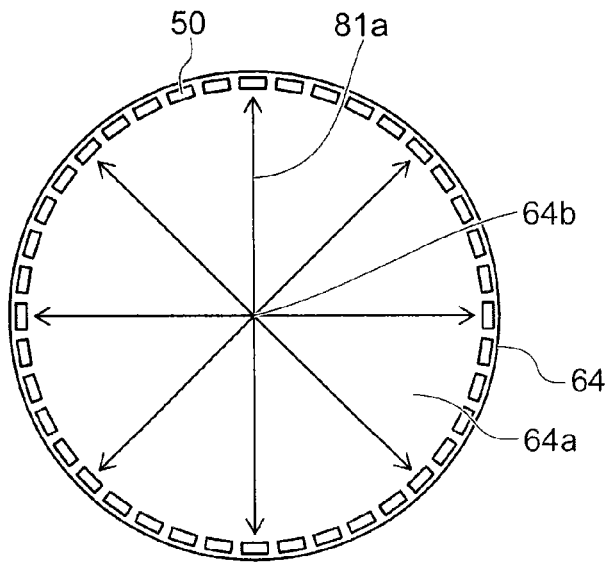
FIGS. 5A to 5C are schematic plan views showing dispositions of the sensing elements 50.
Figure 5B:
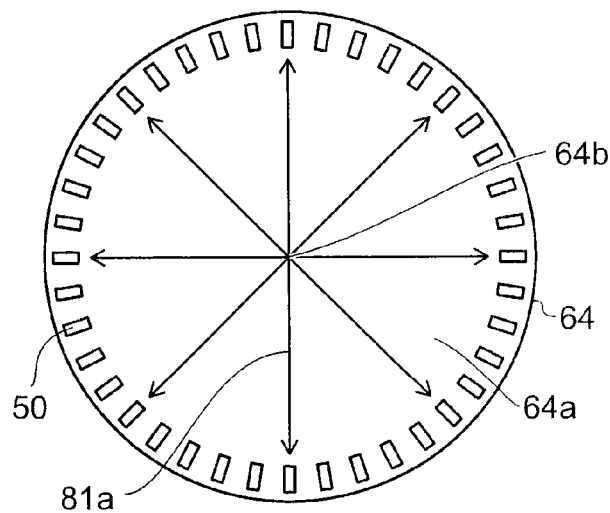
Figure 5C:
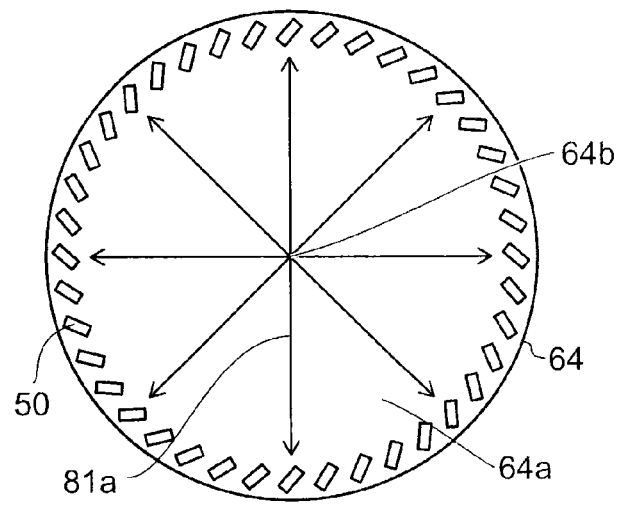

FIGS. 5A to 5C are schematic plan views showing dispositions of the sensing elements 50.

As shown in FIG. 5A, in the case where the planar configuration of the sensing element 50 is a rectangle, the magnetization directions 110 and 120 are directions along the long side of the sensing element 50 due to the shape magnetic anisotropy.

As shown in FIG. 5A, the direction 81a of the stress 81 is a direction extending radially from a centroid 64b of the film unit 64 when an external pressure is applied to the film unit 64.

Although the polarity is different between whether the strain is in the compression direction or the tensile direction, for example, when pressure of some polarity is applied in the case where the sign of the magnetostriction constant of the materials of the first magnetic layer 10 and the second magnetic layer 20 is positive, the magnetization directions 110 and 120 rotate toward the direction 81a of the stress 81. Then, the magnetization direction tilts from the initial magnetization direction (the long-side direction) toward the short-side direction due to the external pressure application.

Therefore, each of the sensing elements 50 has a first surface (e.g., a rectangular long side) and a second surface (e.g., a rectangular short side) that is provided in a direction intersecting the first surface and is shorter than the first surface. Each of the sensing elements 50 is provided radially with respect to the centroid 64b of the film surface 64a such that the first surface faces the centroid 64b side of the film surface 64a of the film unit 64.

In such a case, each of the sensing elements 50 may be provided such that the first surface is orthogonal to a line extending radially from the centroid 64b of the film surface 64a.

Each of the sensing elements 50 may be provided such that at least one selected from the magnetization direction 110 of the first magnetic layer 10 and the magnetization direction 120 of the second magnetic layer 20 is orthogonal to the line extending radially from the centroid 64b of the film surface 64a.

In the case where the planar configuration of the film unit 64 is a circle, each of the sensing elements 50 may be disposed such that the long side of each of the sensing elements 50 is along the circumferential edge of the film unit 64.

It is favorable for the distance from the centroid 64b of the film unit 64 to the centroid of the sensing element 50 to be the same for each of the sensing elements 50.

By such a disposition of the sensing elements 50, the angular difference between the magnetization direction 110a and the magnetization direction 120a after the rotation can be similar for each of the sensing elements 50. In other words, the characteristics related to the stress 81 can be similar for each of the sensing elements 50.

Although the long side is disposed in a direction along the circumferential edge of the film unit 64 in FIG. 5A, a form that is orthogonal to the form of FIG. 5A may be used. For example, as shown in FIG. 5B, the short side may be disposed in the direction along the circumferential edge of the film unit 64.

In such a case, when the external pressure of the same polarity is applied for the same magnetostriction polarity as the form of FIG. 5A, the magnetization direction does not change. The magnetization direction tilts from the long-side direction toward the short-side direction in the case where the magnetostriction polarity is different from that of the form of FIG. 5A and when the application direction of the external pressure is reversely oriented with respect to that of the form of FIG. 5A.

As shown in FIG. 5C, a configuration is possible in which the long side is disposed neither in the direction along the circumferential edge of the film unit 64 nor in the direction that is orthogonal but at some angle (in the case of FIG. 5C, substantially 45 degrees). In FIG. 5A and FIG. 5B, the magnetization direction does not change except in the case where the external pressure has a polarity in one direction. However, in a disposition such as that of FIG. 5C, the magnetization direction changes according to the polarity for external pressure of either a positive or negative polarity. Therefore, this is advantageous in that measurements are possible regardless of the polarity. On the other hand, the dynamic range of the pressure range is reduced. Therefore, it is favorable for the disposition forms of FIGS. 5A to 5C to be used according to the application.

Although the planar configuration of the film unit 64 shown in FIGS. 5A to 5C is a circle, the planar configuration of the film unit 64 is not limited to being a circle.

Figure 6A:
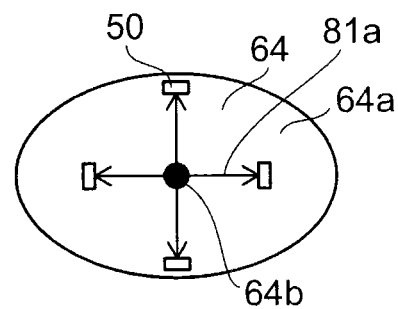
FIGS. 6A to 6C are schematic plan views showing other planar configurations of the film unit 64 and dispositions of the sensing elements 50.
Figure 6B:
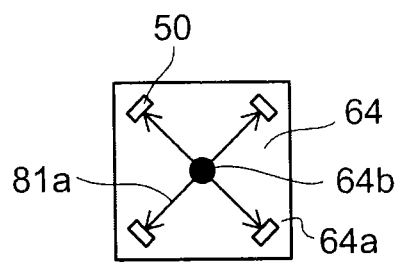
Figure 6C:
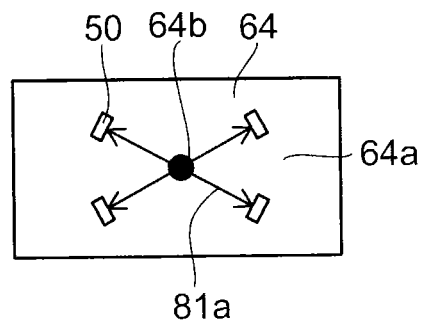

FIGS. 6A to 6C are schematic plan views showing other planar configurations of the film unit 64 and dispositions of the sensing elements 50.

As shown in FIGS. 6A to 6C, the planar configuration of the film unit 64 may be a regular polygon such as an ellipse, a square, a rectangle, etc.

Even in the case of such a planar configuration of the film unit 64, the disposition of the sensing elements 50 may be similar to those described above.

For example, as shown in FIGS. 6A to 6C, each of the sensing elements 50 is provided radially with respect to the centroid 64b of the film surface 64a such that the first surface faces the centroid 64b side of the film surface 64a of the film unit 64.

In such a case, each of the sensing elements 50 may be provided such that the first surface is orthogonal to a line extending radially from the centroid 64b of the film surface 64a.

Each of the sensing elements 50 may be provided such that at least one selected from the magnetization direction 110 of the first magnetic layer 10 and the magnetization direction 120 of the second magnetic layer 20 is orthogonal to a line extending radially from the centroid 64b of the film surface 64a.

In such a case, it is favorable for the distance from the centroid 64b of the film unit 64 to the centroid of the sensing element 50 to be the same for each of the sensing elements 50.

Although the case is shown where four sensing elements 50 are provided as an example, the number of the sensing elements 50 may be modified appropriately.

Effects of the pressure sensor 310 will now be described.

Figure 7A:
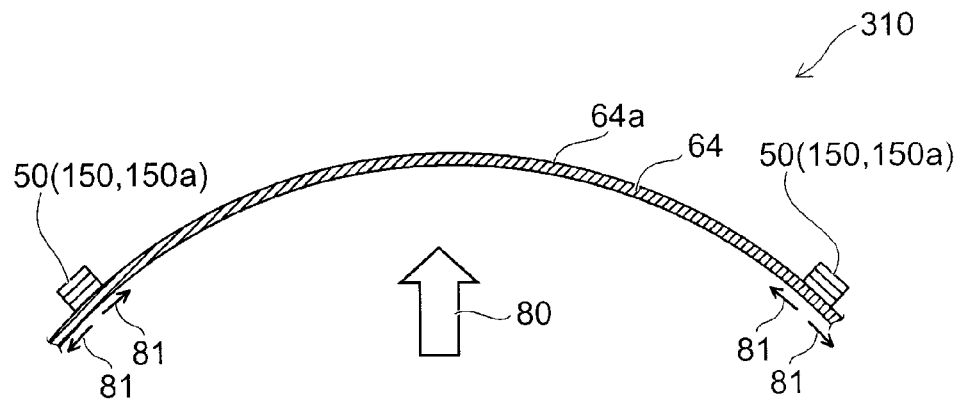
FIGS. 7A to 7C are schematic views showing effects of the pressure sensor 310.
Figure 7B:
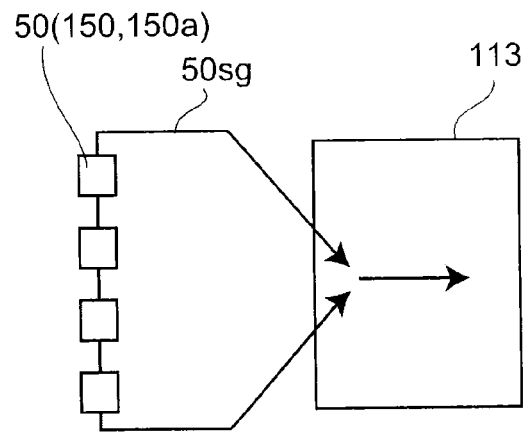
Figure 7C:
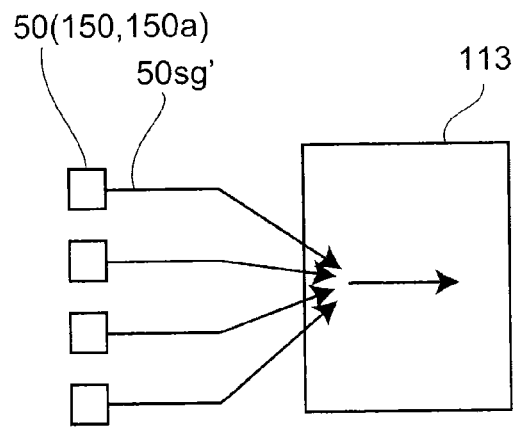

FIGS. 7A to 7C are schematic views showing effects of the pressure sensor 310.

FIG. 7A is a schematic cross-sectional view of a portion including the film unit 64. FIGS. 7B and 7C are schematic views showing signal processing of the pressure sensor 310. FIG. 7B is the case where the sensing elements 50 (150, 150a) are electrically connected in series; and FIG. 7C is the case where the sensing elements 50 (150, 150a) are electrically connected in parallel.

First, when external pressure 80 is applied as shown in FIG. 7A, the film unit 64 is subjected to the external pressure 80 and deflects. For example, the film surface 64a deflects outward in a convex configuration. When the film surface 64a deflects outward in a convex configuration, the stress 81 is applied to the sensing elements 50 (150, 150a). In the case shown in FIG. 7A, a tensile stress is applied to the sensing elements 50 (150, 150a). When the film surface 64a deflects in a concave configuration, a compressive stress is applied to the sensing elements 50 (150, 150a).

When the stress 81 is applied to the sensing elements 50 (150, 150a), the electrical resistance of the sensing elements 50 (150, 150a) changes according to the stress 81 as described above.

In the case where the multiple sensing elements 50 (150, 150a) are connected in series as shown in FIG. 7B, a signal 50sg having a signal voltage that is N times larger according to the number of elements N is sent to a processing circuit 113 as the change amount of the signal. At this time, the thermal noise and the Schottky noise increase by a factor of $\sqrt{N}$ for N elements. That is, the SN ratio (signal-noise ratio (SNR))

increases by a factor of √N when using N sensing elements. It is an effect of the embodiment that the SN ratio can be improved by increasing the number of elements N without increasing the size (the diaphragm size) of the film unit 64.

As described above, the characteristics related to the stress 81 are similar for each of the sensing elements 50 (150, 150a). Therefore, it is possible to simply add each of signals 50sg'.

As described above, the characteristics related to the stress 81 are similar for each of the sensing elements 50 (150, 150a). Therefore, it is unnecessary to perform special processing of the signal 50sg from the multiple sensing elements 50 (150, 150a) that are electrically connected in series.

Here, the bias voltage that can be applied to one sensing element 50 (150, 150a) is about 150 mV. In the case where N sensing elements (N≥2) are electrically connected in series, the voltage across the terminals is 150 mV×N. For example, for the sensing elements in the case where N=25, the bias voltage is 150 mV×25=3.75 V. It is desirable for the absolute value of the voltage across the terminals to be not less than 1 V to be easy to use in the processing of the electronic circuit at stages subsequent to the sensing elements. A large effect can be obtained in the embodiment because the sensing elements 50 that generate the same signal when the pressure is applied are realizable in a configuration in which the sensing elements 50 are connected in series.

On the other hand, a voltage across the terminals that exceeds 10 V is not very desirable in the processing of the electronic circuit at stages subsequent to the sensing elements. Therefore, it is desirable for the bias voltage and the number N of the sensing elements 50 connected in series to be set to have an appropriate voltage range.

For example, in the case where the sensing elements are electrically connected in series, the favorable voltage range of the voltage across the terminals (e.g., the voltage between the two arrows in FIG. 7B) is not less than 1 V and not more than 10 V. In the case where the bias voltage applied to each sensing element 50 is 150 mV, it is desirable for the number of elements N to be not less than 6 and not more than 66 to generate the voltage across the terminals. In the case where the bias voltage applied to each sensing element 50 is 100 mV, it is desirable for the number of elements N to be not less than 10 and not more than 100. In the case where the bias voltage applied to each sensing element 50 is 50 mV, it is desirable for the number of elements N to be not less than 20 and not more than 200.

In such a case, considering the realistic range of the bias voltage while ensuring the reliability of the sensing elements, it is desirable for the number N of the sensing elements 50 that are connected in series to be not less than 6 and not more than 200.

Although an example of a series connection of the N elements to improve the S/N ratio is illustrated in the effect described above, signal processing to improve the frequency characteristics, etc., also is possible by processing the signal 50sg from the multiple sensing elements 50 (150, 150a).

Therefore, highly-sensitive sensing of the pressure in a wide frequency band is possible.

Not only addition but also multiplication, subtraction, etc., may be performed.

Although a form is described above in which all of the N elements are electrically connected in series, a circuit configuration may be implemented in which a portion of the N elements is electrically connected in parallel.

As shown in FIG. 7C, a configuration may be used in which the signal 50sg' corresponding to the change of the electrical resistance is sent individually to the processing circuit 113 from the multiple sensing elements 50 (150, 150a). Each of the signals 50sg' that is sent is processed by the processing circuit 113. For example, each of the signals 50sg' is added.

As described above, the characteristics related to the stress 81 are similar for each of the sensing elements 50 (150, 150a). Therefore, it is possible to simply add each of the signals 50sg'.

The pressure sensor 310 may be used in, for example, a microphone such as an acoustic microphone, an ultrasonic microphone, and the like, a blood pressure sensor, a touch panel, etc. In such a case, it is possible to obtain a sense signal suited to the amplification of the subsequent stages by performing addition of the signals 50sg even in the case where the signal 50sg sent from each of the sensing elements 50 (150, 150a) is faint.

There are cases where the resistance value of the sensing elements 50 (150, 150a) changes when the temperature of the measurement environment changes.

In such a case, temperature compensation can be performed by using a bridge circuit made of the multiple sensing elements 50 (150, 150a).

Figure 8A:
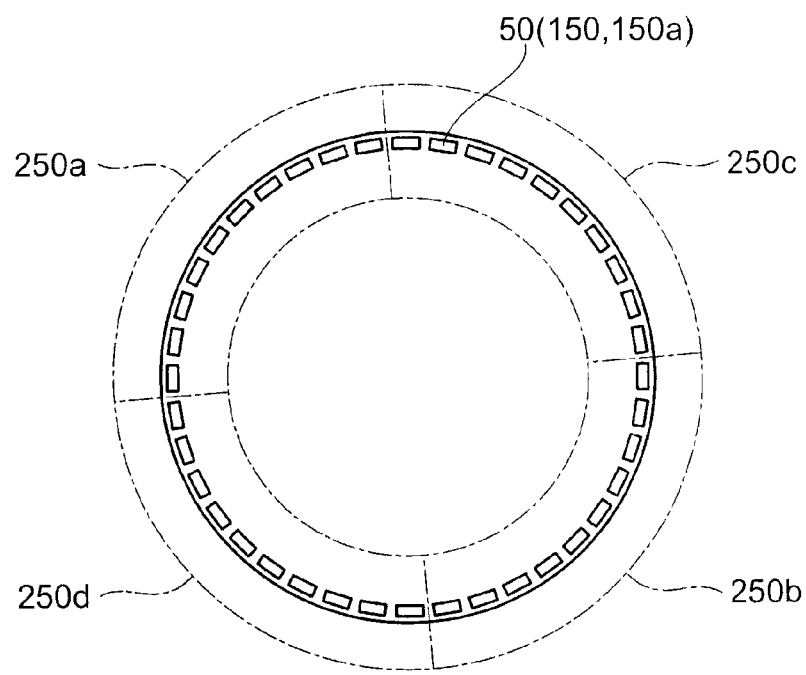
FIGS. 8A and 8B are schematic views showing a bridge circuit made of the multiple sensing elements 50 (150, 150a)
Figure 8B:
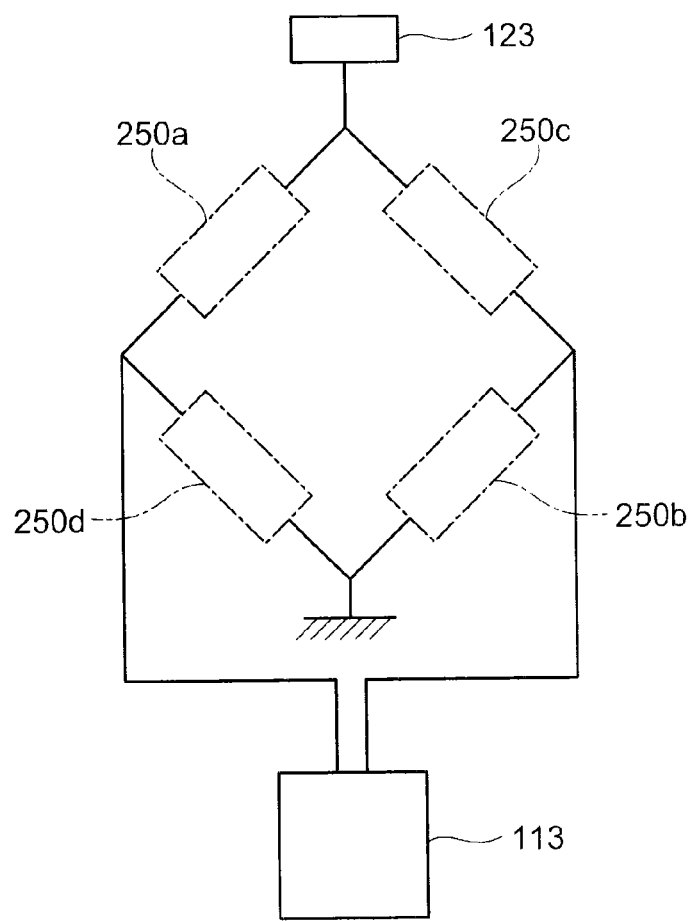

FIGS. 8A and 8B are schematic views showing a bridge circuit made of the multiple sensing elements 50 (150, 150a).

FIG. 8A is a schematic view showing the configuration of the bridge circuit; and FIG. 8B is a circuit diagram.

As shown in FIG. 8A, ten sensing elements 50 (150, 150a) that are electrically connected in series are provided in each of regions 250a to 250d.

Then, a bridge circuit can be made of the multiple sensing elements 50 (150, 150a) by performing connections such as those shown in FIG. 8B.

The number of the sensing elements 50 (150, 150a) in each of the regions 250a to 250d is not limited to ten and may be modified appropriately.

As described above, the characteristics related to the stress 81 are similar for each of the sensing elements 50 (150, 150a). Therefore, the bridge circuit can be formed easily by the number of the sensing elements 50 (150, 150a) being the same in each of the regions 250a to 250d.

A constant current circuit 123 and the processing circuit 113 are electrically connected at prescribed positions of the bridge circuit.

By forming the bridge circuit made of the multiple sensing elements 50 (150, 150a), a high-precision measurement can be performed even in the case where the temperature of the measurement environment fluctuates.

Common mode noise may be removed by forming a differential circuit made of the multiple sensing elements 50 (150, 150a).

By using the pressure sensor 310 as described above, a sense signal that is more suited to the amplification of the subsequent stages can be obtained.

It is difficult to obtain such a sense signal that is suited to the amplification of the subsequent stages using a capacitive pressure sensor or the like.

For example, the sensitivity of a capacitive pressure sensor degrades in the case where the sensing elements are downscaled because the surface area between the electrodes decreases. In a resistive pressure sensor as well, the sensitivity degrades in the case where the sensing elements are downscaled because the current flowing in the resistors which are the sensing elements decreases. Therefore, it is difficult to downscale the sensing elements in capacitive pressure sensors and resistive pressure sensors.

Conversely, the inverse-magnetostriction effect and the magnetoresistance effect are utilized in the sensing elements 50 (150, 150a). In other words, the change of the electrical resistance occurring due to the change of the magnetization direction is sensed. Therefore, the degradation of the sensitivity can be suppressed even in the case where the sensing elements 50 (150, 150a) are downscaled. As a result, a compact and highly-sensitive pressure sensor 310 is possible.

As described below, the sensing elements 50 (150, 150a) may be provided above a substrate on which transistors 132 are formed. Thus, it is possible to downsize the pressure sensor 310; and it is possible to sense the pressure with high sensitivity even in a micro region.

In the case where the film unit 64 is provided above the transistors 132, the range of movement of the film unit 64 (the range where deflecting is possible) may be 10 µm or less.

In such a case, the formation of the film unit 64 is easier if the range of movement of the film unit 64 is reduced further.

However, if the range of movement of the film unit 64 is reduced, it is necessary to increase the sensitivity α of the pressure sensor to accurately sense the pressure.

Also, to accurately sense the pressure even in a micro-contact state, it is necessary to reduce the surface area of the film unit 64.

However, the sensitivity α of the pressure sensor degrades in the case where the surface area of the film unit 64 is reduced without reducing the thickness of the film unit 64 because the deflection amount undesirably becomes small. In such a case, to avoid the pressure sensor breaking easily, the thickness of the film unit 64 cannot be reduced very much. Therefore, there is a risk that the sensitivity α of the pressure sensor may degrade in the case where the surface area of the film unit 64 is reduced.

Therefore, it becomes necessary to increase the sensitivity α of the pressure sensor in the case where the range of movement of the film unit 64 is to be reduced and the surface area of the film unit 64 is to be reduced.

Here, in the case of a piezoresistive strain sensor using silicon, the sensitivity of the sensor is determined by the material that is used; and the sensitivity of the sensor is, for example, about 130. In the case of a piezoresistive strain sensor using silicon, it becomes necessary for the surface area of the element to be such that one side is about 100 µm. Therefore, the sensitivity of the sensor per unit surface area is $130/100 \mu m^2$ which is about $10^{10}$.

Conversely, in the pressure sensor 310 (a spintronic strain sensor), the sensitivity α of the pressure sensor 310 can be increased substantially without depending on the surface area of the sensing elements 50 (150, 150a).

In such a case, the sensitivity α of the pressure sensor 310 is, for example, $\alpha = (\Delta R/R_{min})/\epsilon$. $R_{min}$ is the value of the resistance when the resistance is low; $\Delta R$ is the resistance change amount; and $\epsilon$ is the strain expressed by $\Delta l/l$. Here, $l$ is the initial length; and $\Delta l$ is the displacement amount of the length.

In the case of the pressure sensor 310, there is no upper limit on the sensitivity α; and a sensitivity α of about 1000 can be realized easily. To realize the sensitivity α of about 1000, the necessary surface area of the sensing element 50 (150, 150a) is about 400 $nm^2$. Therefore, the sensitivity α per unit surface area is about $10^{17}$.

In other words, by using the pressure sensor 310, it is possible to improve the sensitivity per unit surface area by a factor of about $10^7$ compared to the case of a piezoresistive strain sensor using silicon (e.g., a pressure sensor having a MEMS (Micro Electro Mechanical Systems) structure using silicon (Si-MEMS)).

Therefore, a compact and highly-sensitive pressure sensor 310 can be realized.

Second Embodiment

Figure 9:
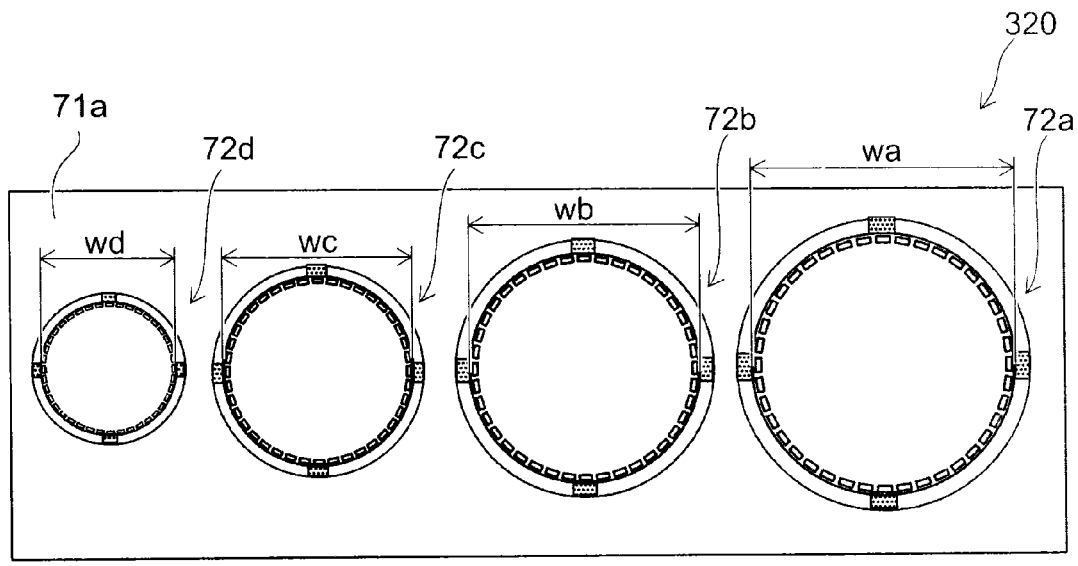
FIG. 9 is a schematic plan view showing the configuration of a pressure sensor 320 according to a second embodiment.

FIG. 9 is a schematic plan view showing the configuration of a pressure sensor 320 according to a second embodiment.

As shown in FIG. 9, the pressure sensor 320 includes sensor units 72a to 72d provided on a base unit 71a.

For example, the sensor unit 72a may be similar to the sensor unit 72 described above.

Although the sensor units 72b to 72d have components similar to those of the sensor unit 72a, diametrical dimensions Wa to Wd of the film unit 64 are different from each other.

In other words, the sensor units 72a to 72d, for which the diametrical dimensions Wa to Wd of the film unit 64 are different from each other, are disposed in an array configuration.

In the case where the diametrical dimensions Wa to Wd of the film unit 64 are different from each other, the resonant frequencies also are different from each other. Therefore, for example, even in the case where the frequency of a sound that is to be measured is the resonant frequency of the sensor unit 72a, the other sensor units 72b to 72d can measure with high precision. In other words, the sensitivity can be improved at multiple resonant frequencies.

Third Embodiment

A method for manufacturing the pressure sensor 310 will now be described.

Figure 10:
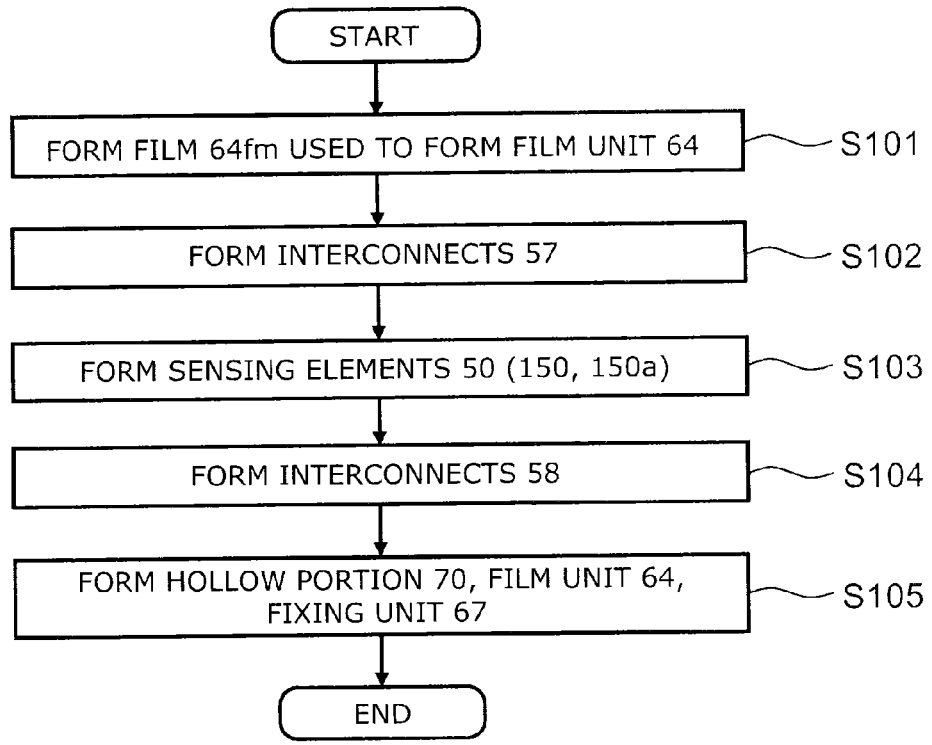
FIG. 10 is a flowchart showing a method for manufacturing the pressure sensor 310 according to a third embodiment.

FIG. 10 is a flowchart showing a method for manufacturing the pressure sensor 310 according to a third embodiment.

FIGS. 11A to 11E are schematic views of processes, showing the method for manufacturing the pressure sensor 310.

In FIGS. 11A to 11E, the configurations and sizes of the components are modified appropriately from those of FIG. 1 for easier viewing of the drawings.

FIG. 11D is a manufacturing method in which the hollow portion 70 is made from the substrate back surface. In the case where this method is used, a SiP (System in Package) configuration is used in which the circuit unit is formed on a separate chip and the pressure sensor and the circuit unit are provided in one package in the mounting process.

Figure 11A:
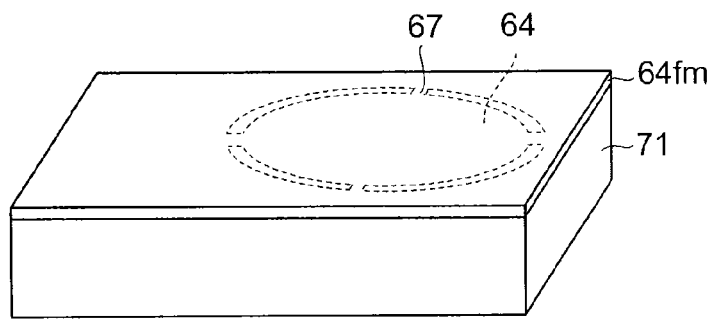
FIGS. 11A to 11E are schematic views of processes, showing the method for manufacturing the pressure sensor 310.
Figure 11B:
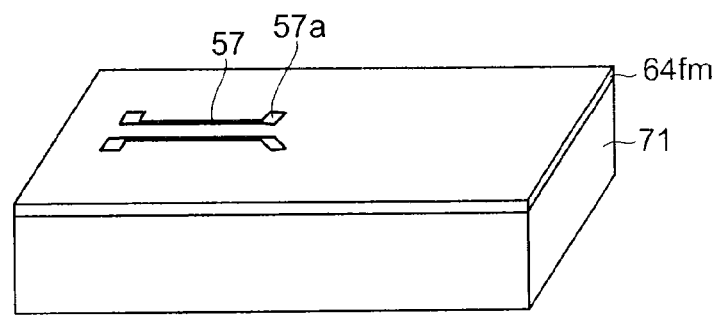
Figure 11C:
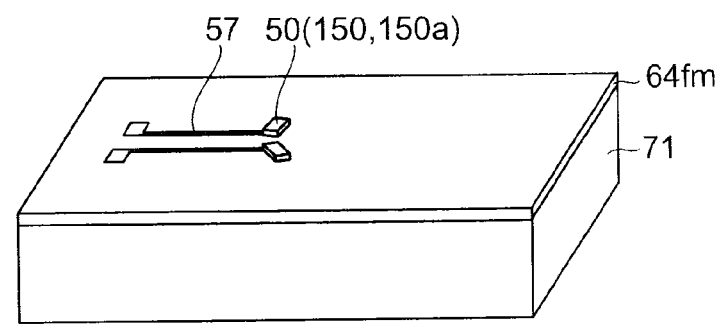
Figure 11D:
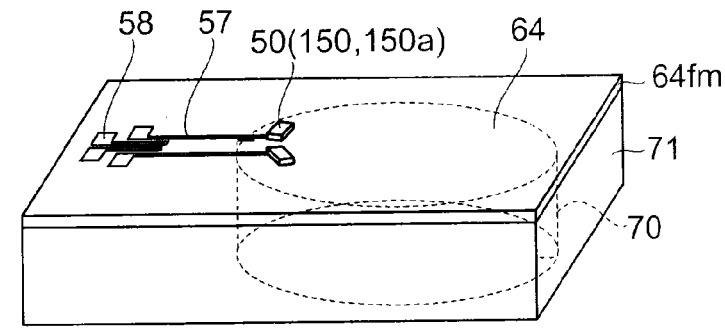
Figure 11E:
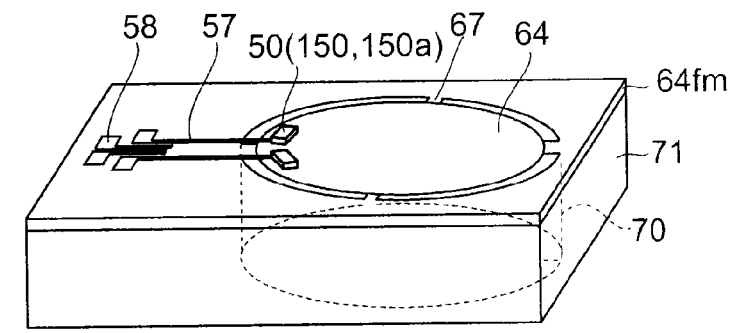

FIG. 11E is a manufacturing method in which the hollow portion 70 is made from the upper portion of the substrate. In the case where this method is used, a SoC (System on Chip) configuration is used in which a CMOS circuit, etc., are provided in the lower portion of the substrate.

First, as shown in FIG. 10, a film 64fm used to form the film unit 64 is formed (step S101).

For example, as shown in FIG. 11A, the film 64fm used to form the film unit 64 is formed on the base unit 71. The base unit 71 may include, for example, a silicon substrate. The film 64fm may include, for example, a silicon oxide film. In the case where the fixing unit 67 that fixes the film unit 64 to the base unit 71 is formed, the fixing unit 67 may be formed in this process by patterning the film 64fm.

Then, the interconnects 57 are formed (step S102).

For example, as shown in FIG. 11B, the interconnects 57 are formed by forming a conductive film on the film 64fm (or the film unit 64) and patterning the conductive film into a prescribed configuration.

In FIG. 11B, a portion of the multiple interconnects 57 is shown for easier viewing of the drawing.

Then, the sensing elements 50 (150, 150a) are formed (step S103).

For example, as shown in FIG. 11C, the sensing elements (150, 150a) are formed on pad portions 57a of the interconnects 57.

For example, a stacked film is formed by forming, in order, the films used to form the components included in the sensing elements 50 (150, 150a). Then, by patterning the stacked film into a prescribed configuration, the sensing elements 50 (150, 150a) are formed.

Then, the interconnects 58 are formed (step S104).

For example, as shown in FIGS. 11D and 11E, a not-shown insulating film is formed to cover the sensing elements 50 (150, 150a); and the upper surfaces of the sensing elements 50 (150, 150a) are exposed by removing a portion of the insulating film. The interconnects 58 are formed by forming a conductive film on the upper surfaces and patterning the conductive film into a prescribed configuration.

At least a portion of steps S102 to S104 may be implemented simultaneously within the extent of technical feasibility; and the order of at least a portion of steps S102 to S104 may be interchanged.

Then, the hollow portion 70, the film unit 64, and the fixing unit 67 are formed (step S105).

For example, as shown in FIGS. 11D and 11E, the hollow portion 70 is made by etching from the back surface (the lower surface) side of the base unit 71. The portion where the hollow portion 70 is not made is the non-hollow portion where the film unit 64 and the fixing unit 67 are formed.

The etching may be performed by, for example, deep RIE (reactive ion etching), the Bosch process, etc.

Fourth Embodiment

Figure 12:
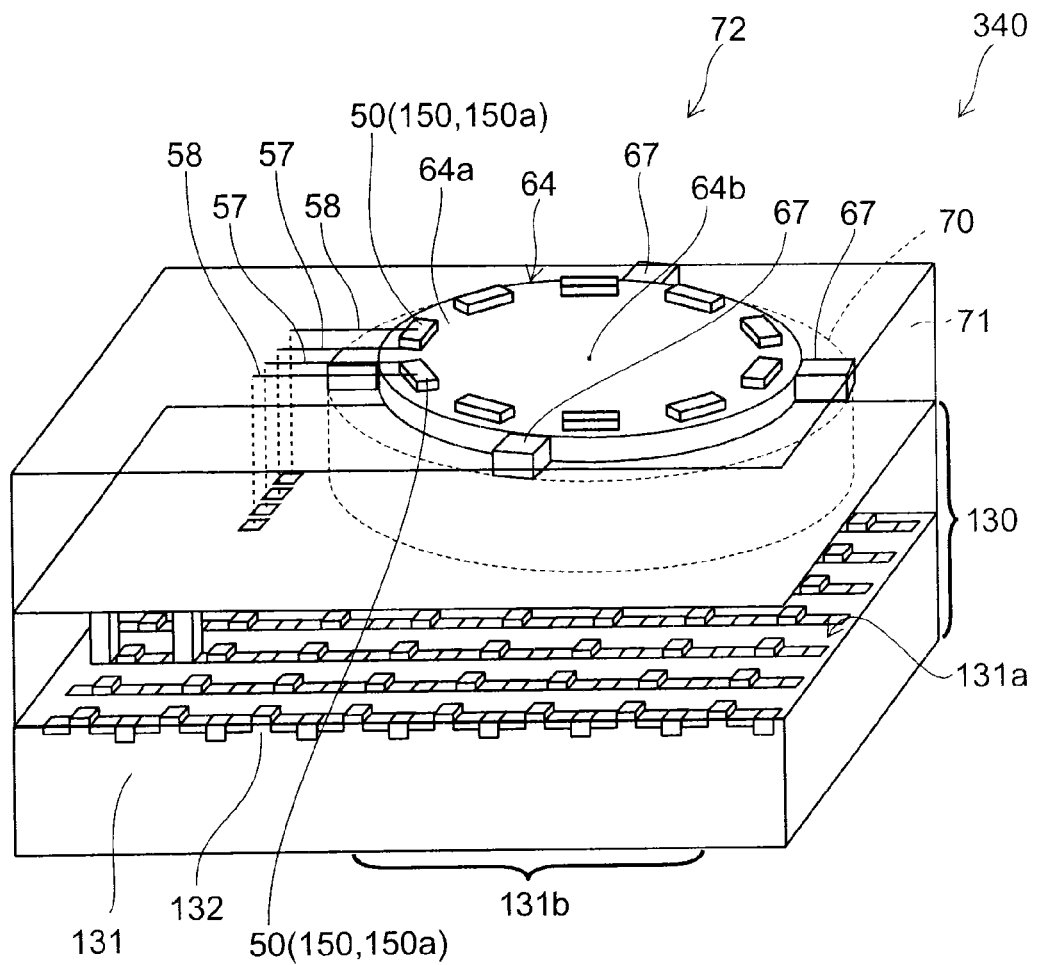
FIG. 12 is a schematic perspective view showing a pressure sensor 340 according to a fourth embodiment.

FIG. 12 is a schematic perspective view showing a pressure sensor 340 according to a fourth embodiment.

As shown in FIG. 12, the sensor unit 72, the base unit 71, and a semiconductor circuit unit 130 are provided in the pressure sensor 340.

The semiconductor circuit unit 130 is provided below the base unit 71.

The semiconductor circuit unit 130 includes, for example, a semiconductor substrate 131 and the transistors 132.

An element region 131b is provided at a major surface 131a of the semiconductor substrate 131. The transistors 132 are provided in the element region 131b.

The semiconductor circuit unit 130 may include the processing circuit 113. The processing circuit 113 may be provided in the element region 131b or may be provided in a region other than the element region 131b. The processing circuit 113 may be provided at any location of the semiconductor circuit unit 130. The processing circuit 113 may include the transistors 132 provided in the element region 131b.

The hollow portion 70 is provided above the element region 131b. The sensing elements 50 are provided above the transistors 132.

The transistors 132 and the sensing elements 50 (150, 150a) are electrically connected not by wires but by an interconnect layer formed by a semiconductor manufacturing process. Thus, the pressure can be sensed with high sensitivity in a micro region because it is possible to downsize the pressure sensor 340.

The system as an entirety can be downsized because the sensing elements 50 (150, 150a), the processing circuit 113, the amplifier circuit, the communication circuit, etc., can be provided on a common substrate. It is also possible to reduce the power consumption.

The semiconductor circuit unit 130, the base unit 71, and the sensor unit 72 may be provided integrally; or the semiconductor circuit unit 130, the base unit 71, and the sensor unit 72 may be provided separately. For example, the semiconductor circuit unit 130, the base unit 71, and the sensor unit 72 may be provided on one semiconductor chip as a system-on-a-chip; or the semiconductor circuit unit 130, the base unit 71, and the sensor unit 72 may be provided inside one package as a system in package.

Fifth Embodiment

Figure 13A:
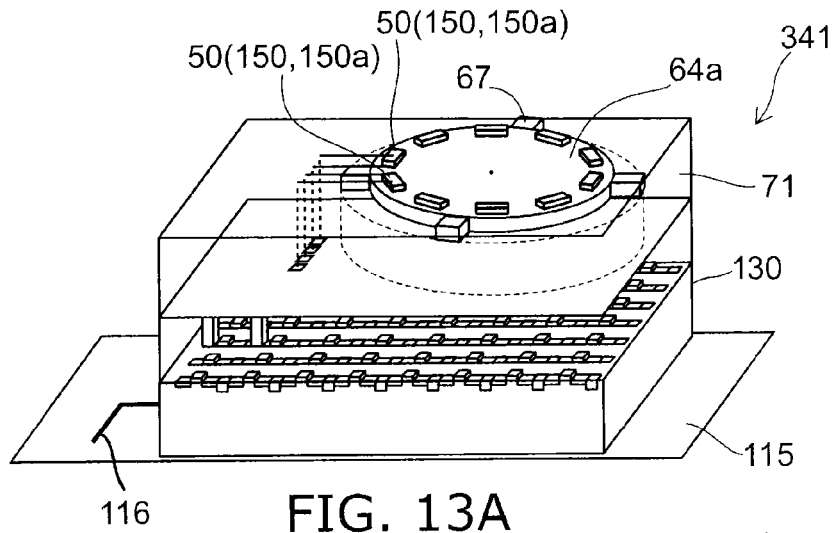
FIGS. 13A to 13C are schematic views showing the configuration of a pressure sensor 341 according to a fifth embodiment.
Figure 13B:
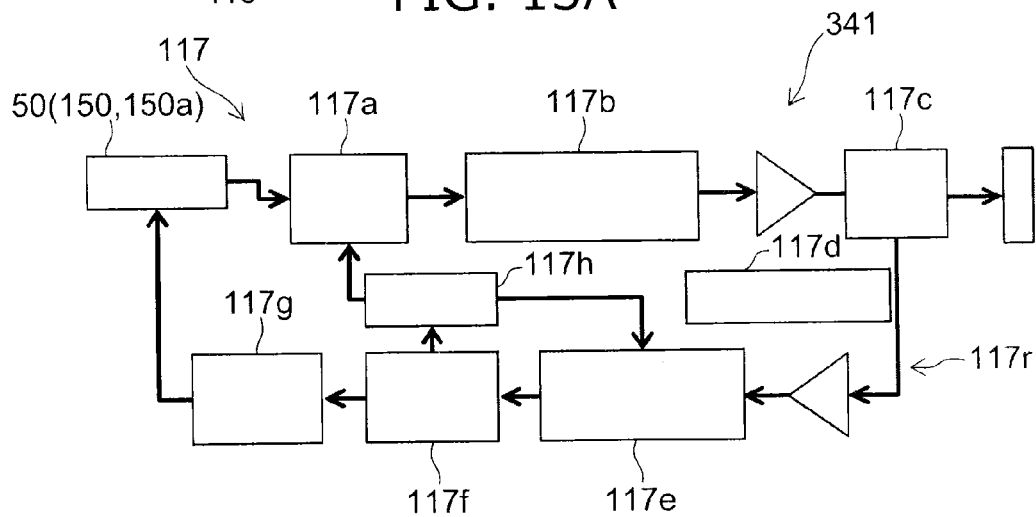
Figure 13C:
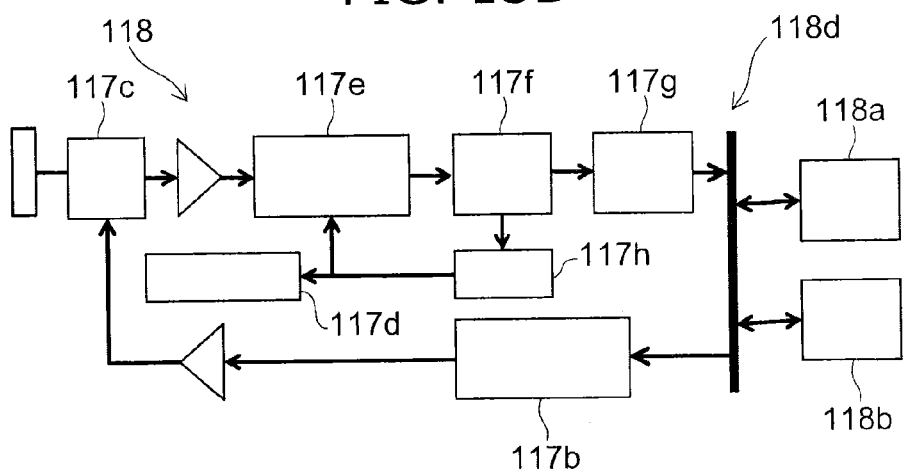

FIGS. 13A to 13C are schematic views showing the configuration of a pressure sensor 341 according to a fifth embodiment.

FIG. 13A is a schematic perspective view; and FIG. 13B and FIG. 13C are block diagrams showing the configuration of the pressure sensor 341.

As shown in FIGS. 13A and 13B, the base unit 71, the sensor unit 72, the semiconductor circuit unit 130, an antenna 115, an electrical interconnect 116, a transmitting circuit 117, and a receiving circuit 117r are provided in the pressure sensor 341.

The antenna 115 is electrically connected to the semiconductor circuit unit 130 via the electrical interconnect 116.

The transmitting circuit 117 wirelessly transmits data based on the electrical signal flowing in the sensing elements 50 (150, 150a). At least a portion of the transmitting circuit 117 may be provided in the semiconductor circuit unit 130.

The receiving circuit 117r receives a control signal from an electronic device 118d. At least a portion of the receiving circuit 117r may be provided in the semiconductor circuit unit 130. By providing the receiving circuit 117r, for example, the operation of the pressure sensor 341 can be controlled by operating the electronic device 118d.

As shown in FIG. 13B, for example, a Manchester encoding unit 117b and an AD converter 117a that is connected to the sensing elements 50 (150, 150a) may be provided in the transmitting circuit 117. The transmitting and the receiving may be switched by providing a switching unit 117c. In such a case, a timing controller 117d may be provided; and the switching of the switching unit 117c may be controlled by the timing controller 117d. A data correcting unit 117e, a synchronizing unit 117f, a determining unit 117g, and a voltage-controlled oscillator (VCO) 117h also may be provided.

As shown in FIG. 13C, a receiving unit 118 is provided in the electronic device 118d that is used in combination with the pressure sensor 341. Examples of the electronic device 118d include, for example, electronic devices such as portable terminals, etc.

In such a case, the pressure sensor 341 that includes the transmitting circuit 117 and the electronic device 118d that includes the receiving unit 118 can be used in combination.

The Manchester encoding unit 117b, the switching unit 117c, the timing controller 117d, the data correcting unit 117e, the synchronizing unit 117f, the determining unit 117g, the voltage-controlled oscillator 117h, a memory unit 118a, and a central processing unit (CPU) 118b may be provided in the electronic device 118d.

Sixth Embodiment

The method for manufacturing the pressure sensor 340 shown in FIG. 12 will now be described.

FIG. 14A, FIG. 14B, FIG. 15A, FIG. 15B, FIG. 16A, FIG. 16B, FIG. 17A, FIG. 17B, FIG. 18A, FIG. 18B, FIG. 19A, FIG. 19B, FIG. 20A, FIG. 20B, FIG. 21A, FIG. 21B, FIG. 22A, FIG. 22B, FIG. 23A, FIG. 23B, FIG. 24A, FIG. 24B, FIG. 25A, and FIG. 25B are schematic views showing a method for manufacturing the pressure sensor 340 according to a sixth embodiment.

FIG. 14A to FIG. 25A are schematic plan views; and FIG. 14B to FIG. 25B are schematic cross-sectional views.

Arrows X, Y, and Z in the drawings illustrate directions that are orthogonal to each other.

Figure 14A:
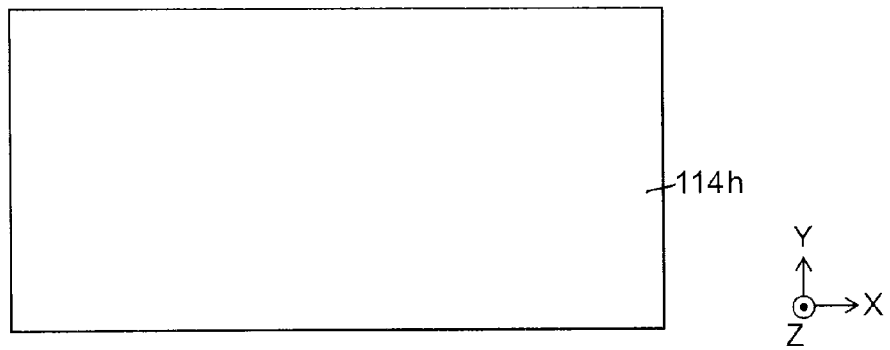
FIG. 14A, FIG. 14B, FIG. 15A, FIG. 15B, FIG. 16A, FIG. 16B, FIG. 17A, FIG. 17B, FIG. 18A, FIG. 18B, FIG. 19A, FIG. 19B, FIG. 20A, FIG. 20B, FIG. 21A, FIG. 21B, FIG. 22A, FIG. 22B, FIG. 23A, FIG. 23B, FIG. 24A, FIG. 24B, FIG. 25A, and FIG. 25B are schematic views showing a method for manufacturing the pressure sensor 340 according to a sixth embodiment.
Figure 14B:
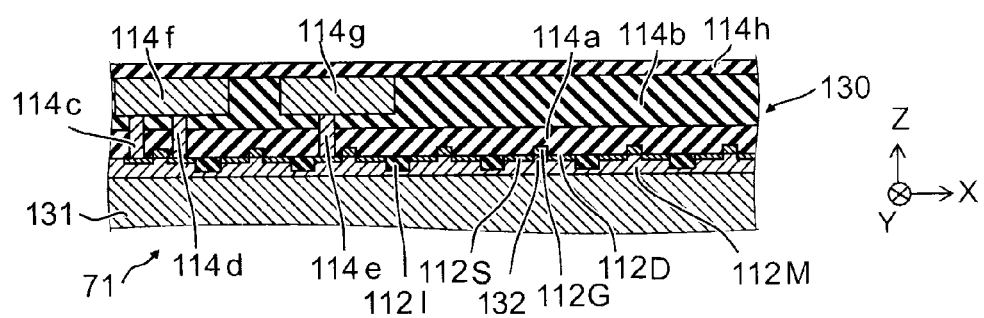

First, as shown in FIGS. 14A and 14B, a semiconductor layer 112M is formed in the front surface portion of the semiconductor substrate 131. Continuing, an element-separating insulation layer 112I is formed in the upper surface of the semiconductor layer 112M. Then, gates 112G are formed on the semiconductor layer 112M with a not-shown insulating layer interposed. Continuing, the transistors 132 are formed by forming a source 112S and a drain 112D on two sides of each of the gates 112G. Continuing, an inter-layer insulating film 114a is formed on the transistors 132; and an inter-layer insulating film 114b is formed on the inter-layer insulating film 114a.

Then, trenches and holes are made in a portion of the inter-layer insulating films 114a and 114b in the region to be used as the non-hollow portion. Continuing, connecting pillars 114c to 114e are formed by filling a conductive material into the holes. In such a case, for example, the connecting pillar 114c is electrically connected to the source 112S of one of the transistors 132; and the connecting pillar 114d is electrically connected to the drain 112D. For example, the connecting pillar 114e is electrically connected to the source 112S of one other of the transistors 132. Continuing, interconnect units 114f and 114g are formed by filling a conductive material into the trenches. The interconnect unit 114f is electrically connected to the connecting pillar 114c and the connecting pillar 114d. The interconnect unit 114g is electrically connected to the connecting pillar 114e. Continuing, an inter-layer insulating film 114h is formed on the inter-layer insulating film 114b.

Figure 15A:
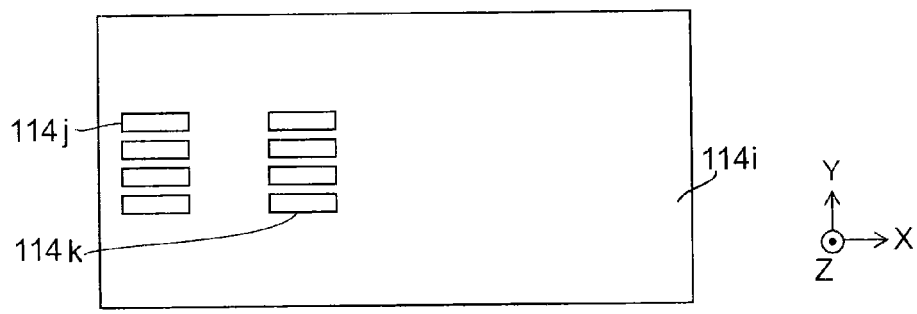
Figure 15B:
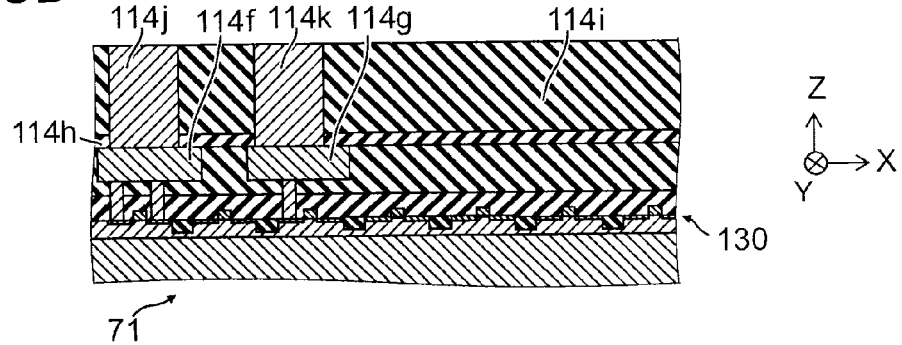

Then, as shown in FIGS. 15A and 15B, an inter-layer insulating film 114i made of silicon oxide (SiO$_2$) is formed on the inter-layer insulating film 114h by, for example, CVD (Chemical Vapor Deposition). Continuing, holes are made at prescribed positions of the inter-layer insulating film 114i; a conductive material (e.g., a metal material) is filled; and the upper surface is planarized by CMP (Chemical Mechanical Polishing). Thereby, a connecting pillar 114j connected to the interconnect unit 114f and a connecting pillar 114k connected to the interconnect unit 114g are formed.

Figure 16A:
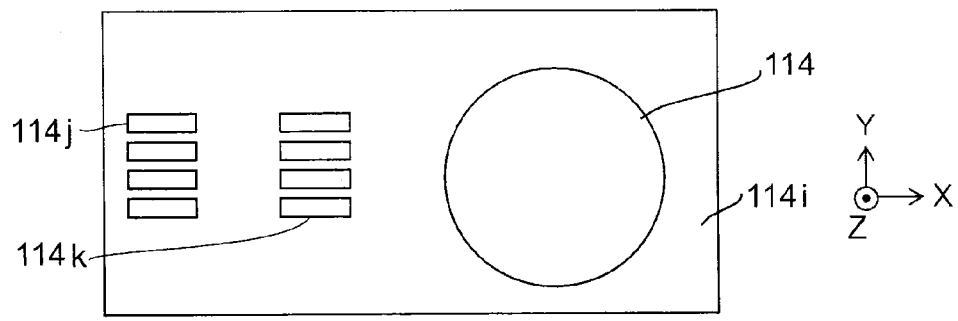
Figure 16B:
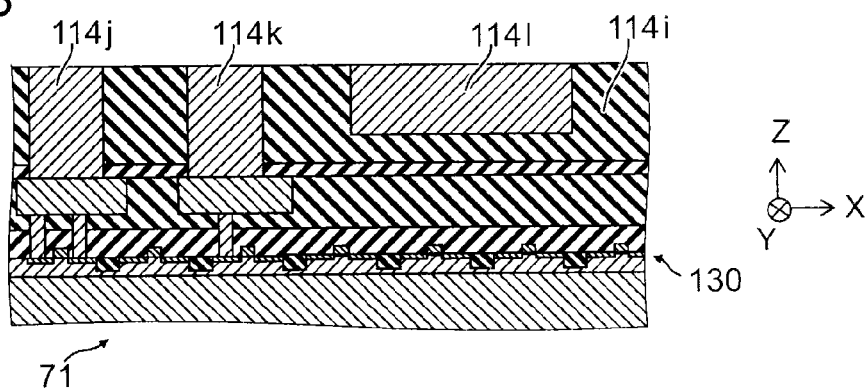

Then, as shown in FIGS. 16A and 16B, a recess is made in the region that becomes the hollow portion 70 of the inter-layer insulating film 114i; and a sacrificial layer 114l is filled into the recess. The sacrificial layer 114l may be formed of, for example, a material that can be formed at a low temperature. The material that can be formed at a low temperature is, for example, silicon-germanium (SiGe), etc.

Figure 17A:
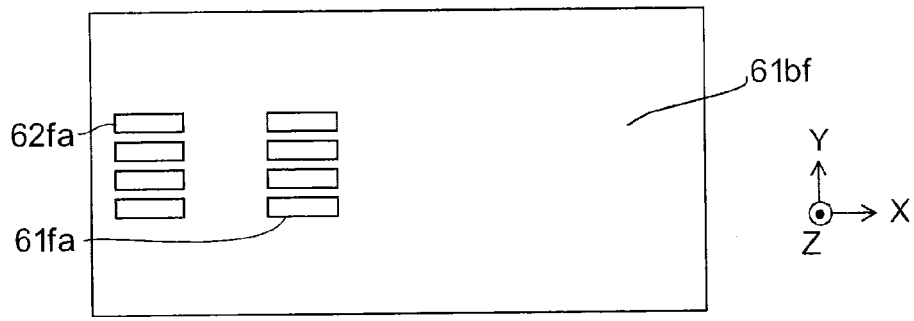
Figure 17B:
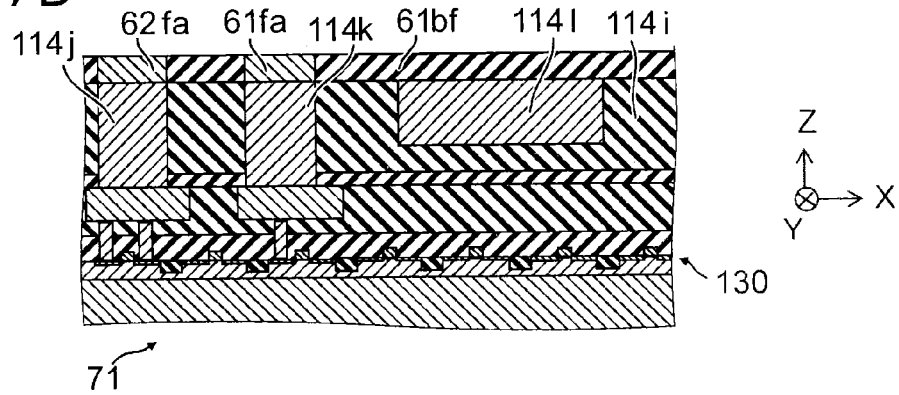

Continuing as shown in FIGS. 17A and 17B, an insulating film 61bf used to form the film unit 64 is formed on the inter-layer insulating film 114i and the sacrificial layer 114l. The insulating film 61bf may be formed of, for example, silicon oxide (SiO$_2$), etc. A connecting pillar 61fa and a connecting pillar 62fa are formed by providing multiple holes in the insulating film 61bf and filling a conductive material (e.g., a metal material) into the multiple holes. The connecting pillar 61fa is electrically connected to the connecting pillar 114k; and the connecting pillar 62fa is electrically connected to the connecting pillar 114j.

Figure 18A:
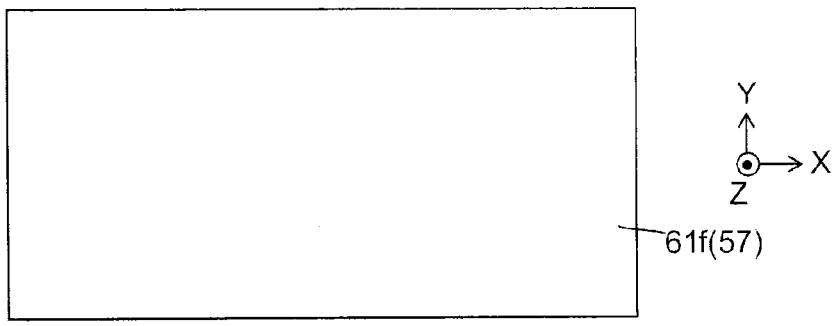
Figure 18B:
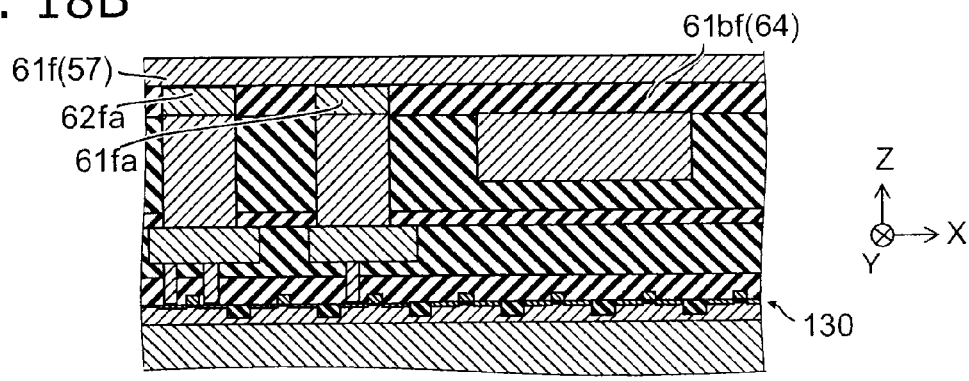

Continuing as shown in FIGS. 18A and 18B, a conductive layer 61f used to form the interconnects 57 is formed on the insulating film 61bf, the connecting pillar 61fa, and the connecting pillar 62fa.

Figure 19A:
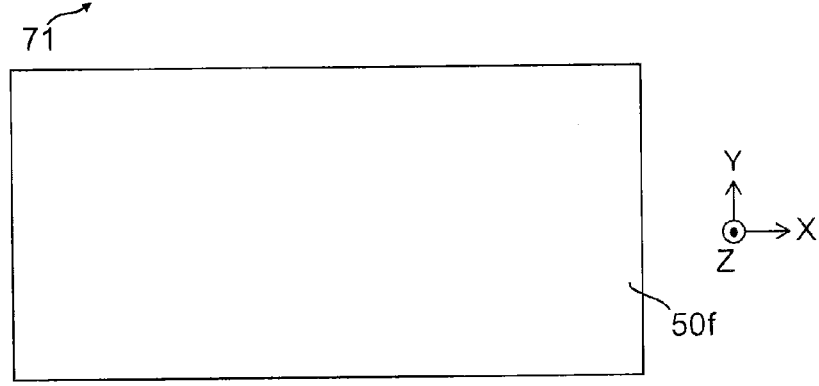
Figure 19B:
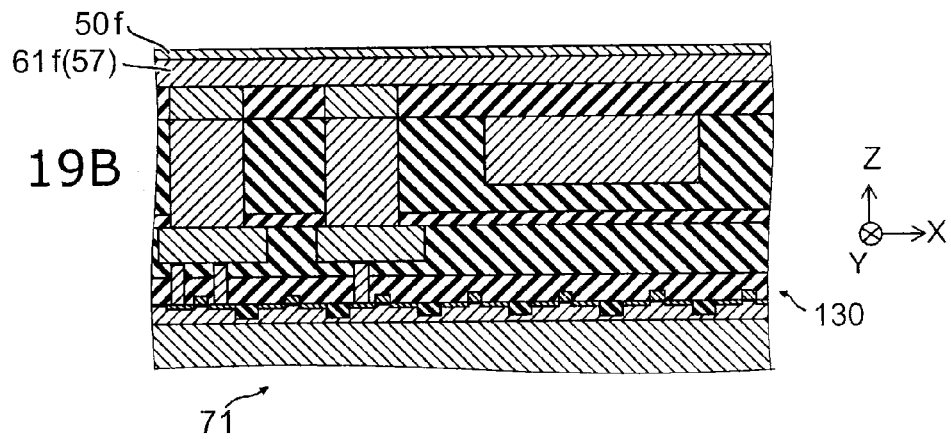

Then, as shown in FIGS. 19A and 19B, a stacked film 50f used to form the sensing elements 50 is formed on the conductive layer 61f.

Hereinbelow, the case where the sensing element 50 is formed is described as an example. Cases where the sensing elements 150 and 150a are formed may be similar. For example, it is sufficient to form the sensing elements 150 and 150a by forming a stacked film by forming, in order, films used to form the components included in the sensing elements 150 and 150a and patterning the stacked film into a prescribed configuration.

Figure 20A:
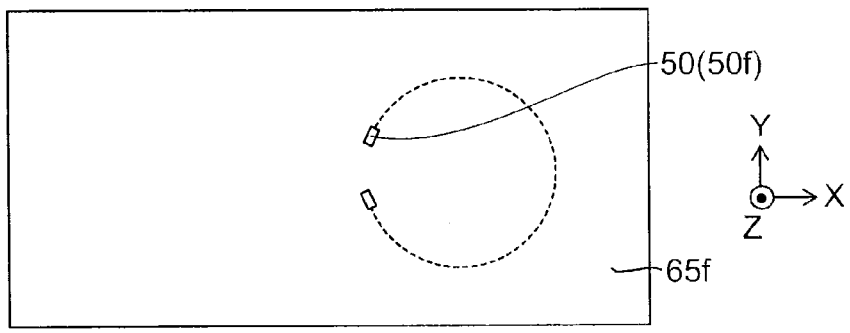
Figure 20B:
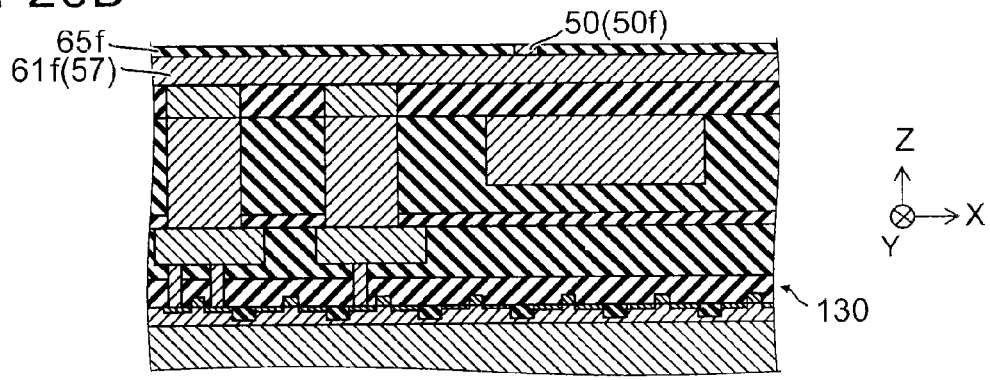

Then, as shown in FIGS. 20A and 20B, the stacked film 50f is patterned into a prescribed configuration; and an insulating film 65f used to form an insulating layer 65 is formed on the stacked film 50f. The insulating film 65f may be formed of, for example, silicon oxide (SiO$_2$), etc.

Figure 21A:
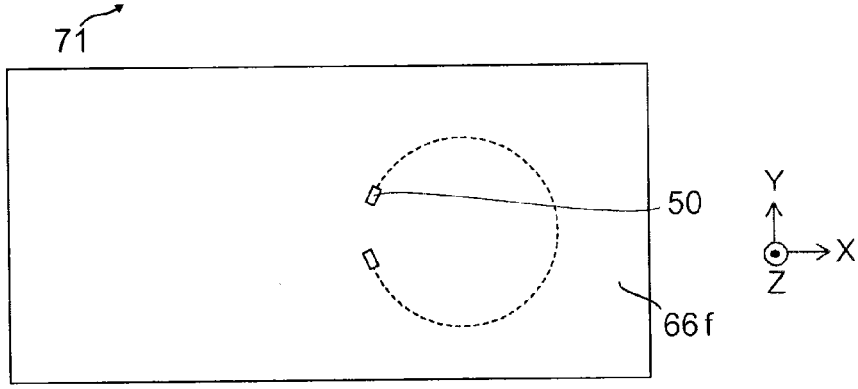
Figure 21B:
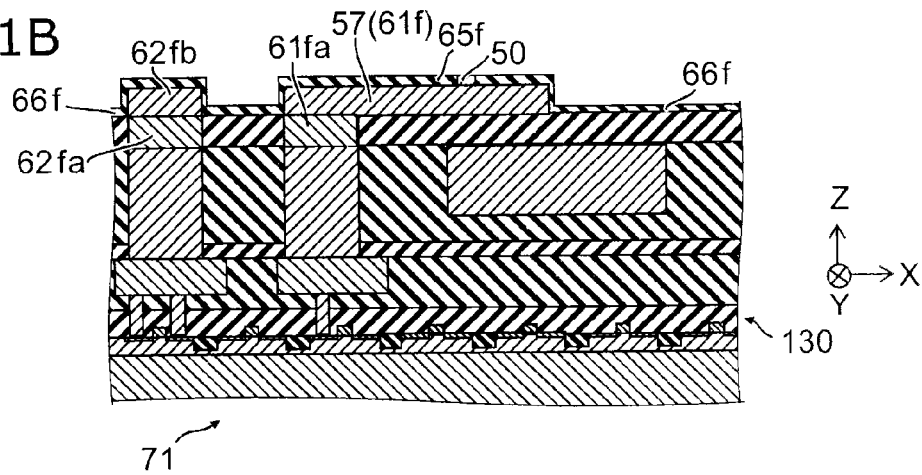

Continuing as shown in FIGS. 21A and 21B, a portion of the insulating film 65f is removed; and the conductive layer 61f is patterned into a prescribed configuration. Thereby, the interconnects 57 are formed. At this time, a portion of the conductive layer 61f is used to form a connecting pillar 62fb that is electrically connected to the connecting pillar 62fa. An insulating film 66f used to form an insulating layer 66 is formed on the conductive layer 61f.

Figure 22A:
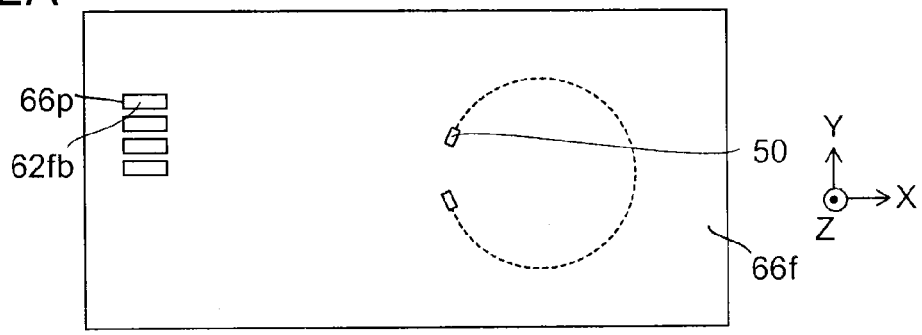
Figure 22B:
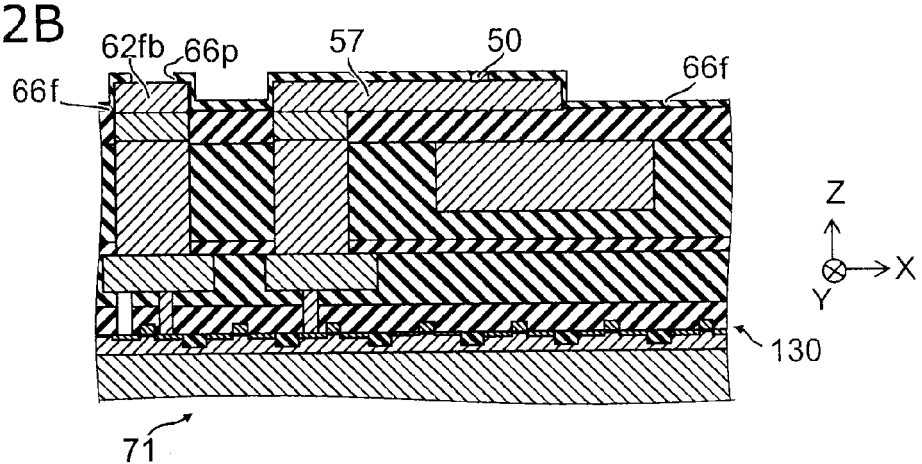

Then, as shown in FIGS. 22A and 22B, an opening 66p is made in the insulating film 66f. Thereby, the connecting pillar 62fb is exposed.

Figure 23A:
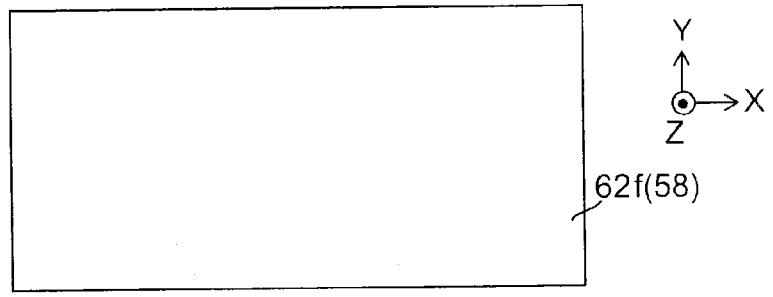
Figure 23B:
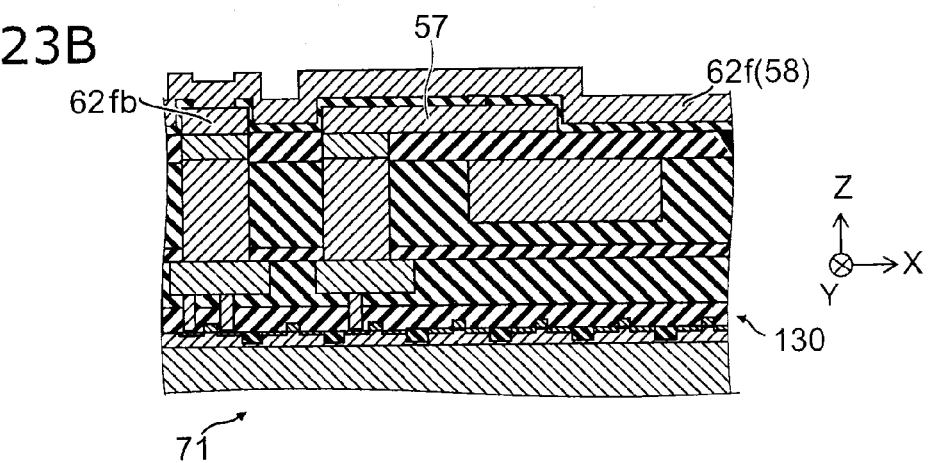

Continuing as shown in FIGS. 23A and 23B, a conductive layer 62f used to form the interconnects 58 is formed at the upper surface. A portion of the conductive layer 62f is electrically connected to the connecting pillar 62fb.

Figure 24A:
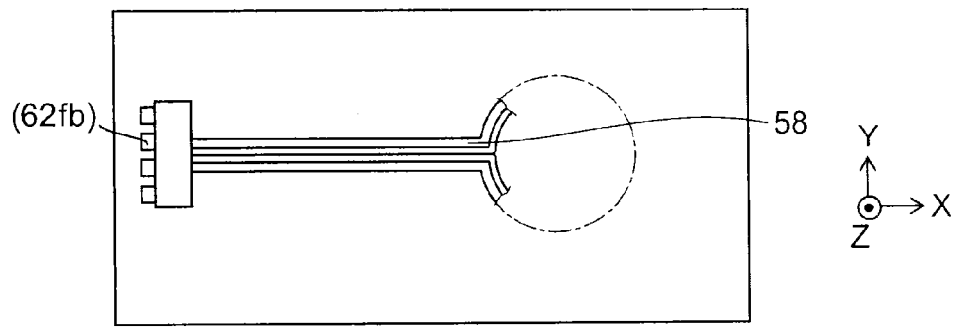
Figure 24B:
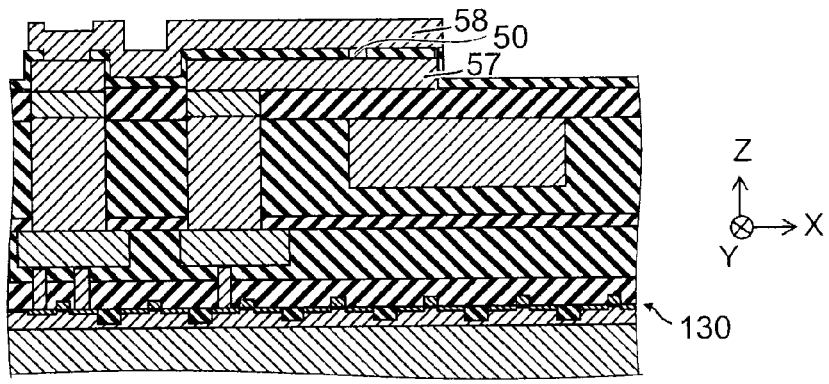

Then, as shown in FIGS. 24A and 24B, the conductive layer 62f is patterned into a prescribed configuration. Thereby, the interconnects 58 are formed. The interconnects 58 are electrically connected to the connecting pillar 62fb.

Figure 25A:
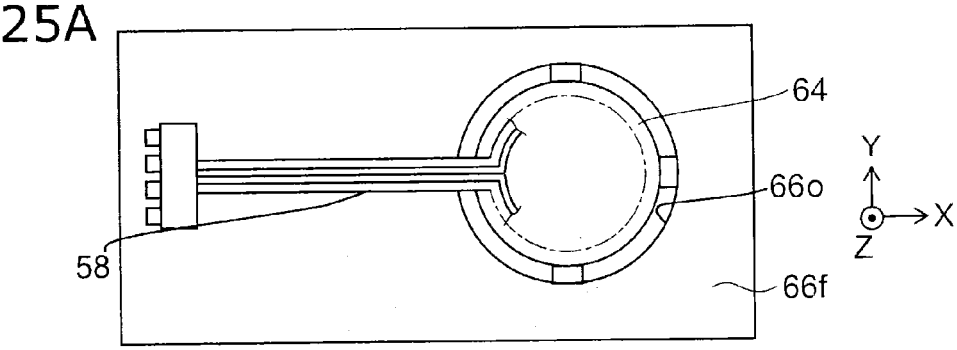
Figure 25B:
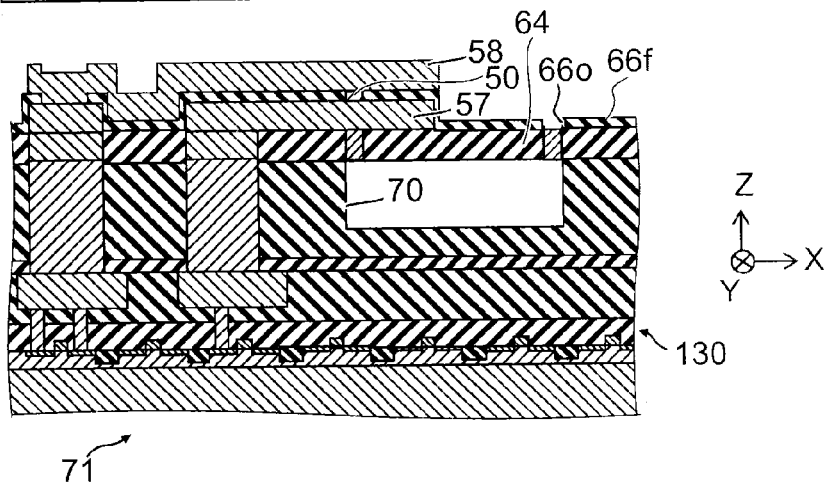

Continuing as shown in FIGS. 25A and 25B, an opening 66o is made in the insulating film 66f in a prescribed configuration. The insulating film 61bf is patterned via the opening 66o; and the sacrificial layer 114l is removed via the opening 66o. Thereby, the hollow portion 70 is made. The removal of the sacrificial layer 114l can be performed by, for example, wet etching.

For example, to form the fixing unit 67 in a ring, it is sufficient to fill the space between the edge of the non-hollow portion and the film unit 64 above the hollow portion 70 with an insulating film.

Thus, the pressure sensor 340 is formed.

Figure 26:
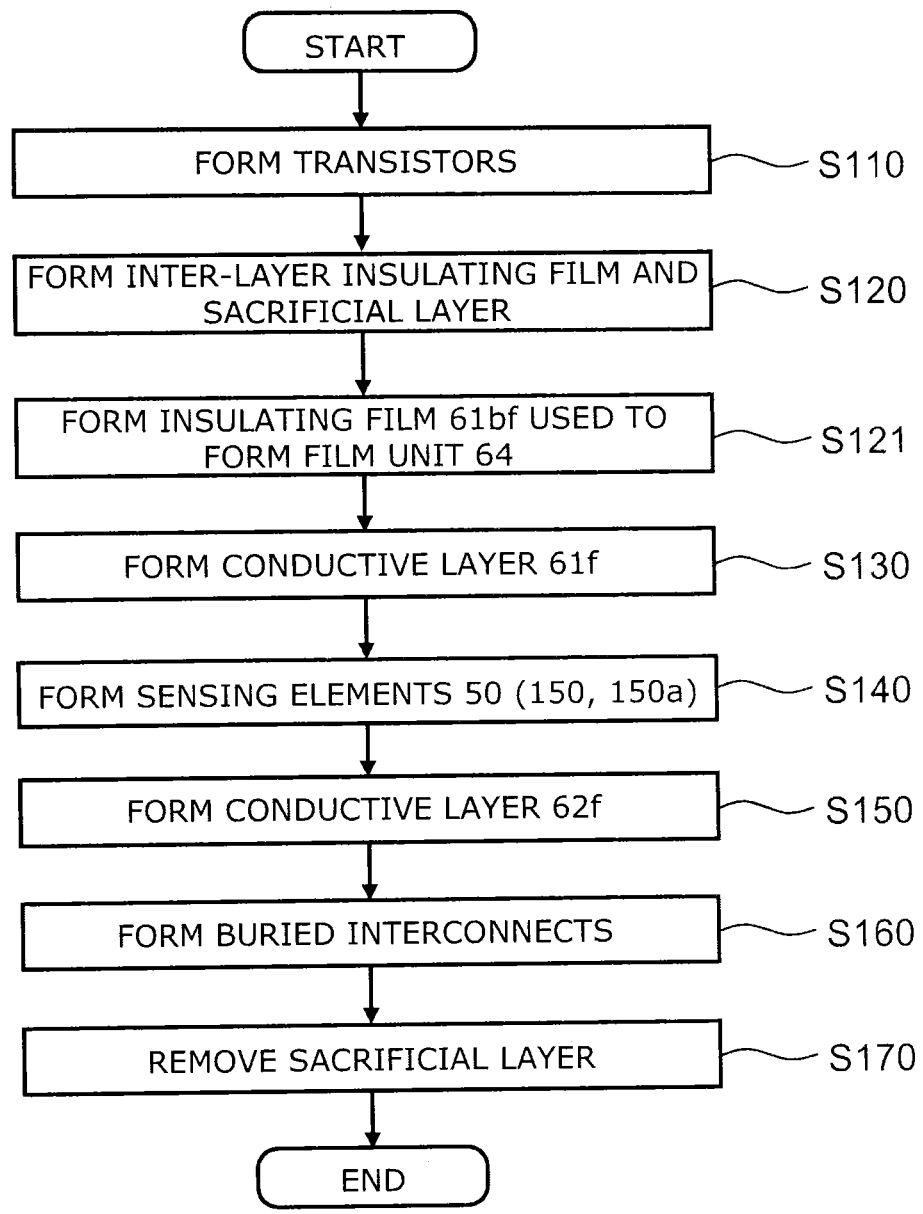
FIG. 26 is a flowchart showing the method for manufacturing the pressure sensor 340 according to the sixth embodiment.

FIG. 26 is a flowchart showing the method for manufacturing the pressure sensor 340 according to the sixth embodiment.

Namely, FIG. 26 is a flowchart of the method for manufacturing the pressure sensor 340 shown in FIG. 14A to FIG. 25B.

First, as shown in FIG. 26, the transistors 132 are formed on the semiconductor substrate 131 (step S110).

For example, the transistors 132 are formed as shown in FIGS. 14A and 14B.

Then, an inter-layer insulating layer is formed on the semiconductor substrate 131; and the sacrificial layer 114l is formed on the transistors 132 (step S120).

For example, the inter-layer insulating layer and the sacrificial layer 114l are formed as shown in FIG. 15A to FIG. 16B. The inter-layer insulating layer includes, for example, the inter-layer insulating film 114i.

Then, the insulating film 61bf used to form the film unit 64 is formed on the inter-layer insulating layer (e.g., the inter-layer insulating film 114i) and the sacrificial layer 114l (step S121).

There are cases where the conductive layer 61f recited below also is used as the film unit 64. In such a case, step S121 is omitted.

Then, the conductive layer 61f used to form the interconnects 57 is formed (step S130).

For example, the conductive layer 61f is formed as shown in FIGS. 18A and 18B.

Then, the sensing elements 50 including the first magnetic layer 10 are formed on the conductive layer 61f above the sacrificial layer 114l (step S140).

For example, the sensing elements 50 are formed as shown in FIG. 19A to FIG. 20B. The sensing elements 150 and 150a also may be formed similarly.

Then, the conductive layer 62f used to form the interconnects 58 is formed on the sensing elements 50 (150, 150a) (step S150).

For example, the conductive layer 62f is formed as shown in FIG. 23A to FIG. 24B.

Continuing, buried interconnects are formed (step S160).

For example, the interconnects that electrically connect the conductive layer 61f to the semiconductor substrate 131 and the interconnects that electrically connect the conductive layer 62f to the semiconductor substrate 131 are formed inside the inter-layer insulating layer.

For example, the buried interconnects are formed as shown in FIG. 14A, FIG. 14B, FIG. 15A, FIG. 15B, FIG. 17A, FIG. 17B, FIG. 21A, and FIG. 21B.

Step S160 may be implemented, for example, once or multiple times in at least one process between step S110 to step S150 and/or after step S150.

Then, the sacrificial layer 114l is removed (step S170).

For example, the sacrificial layer 114l is removed as shown in FIGS. 25A and 25B.

Thus, the pressure sensor 340 is formed.

The content of the processes may be similar to that shown in FIG. 14A to FIG. 25B, and a detailed description is therefore omitted.

Seventh Embodiment

Figure 27:
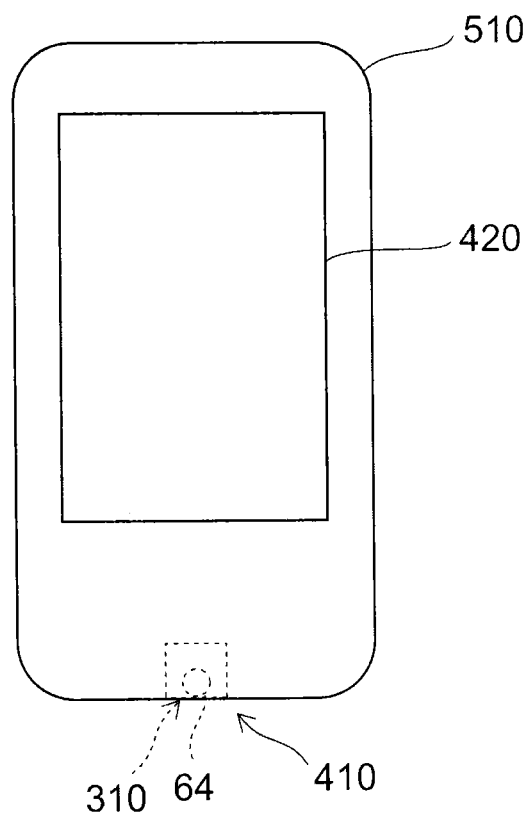
FIG. 27 is a schematic view showing a microphone 410 according to a seventh embodiment.

FIG. 27 is a schematic view showing a microphone 410 according to a seventh embodiment.

As shown in FIG. 27, the microphone 410 includes any pressure sensor (e.g., the pressure sensors 310, 320, 340, or 341) according to the embodiments described above or a pressure sensor according to a modification of these pressure sensors. The microphone 410 that includes the pressure sensor 310 will now be described as an example.

The microphone 410 is embedded in the end portion of a personal digital assistant 510. The film unit 64 of the pressure sensor 310 provided in the microphone 410 may be substantially parallel to, for example, the surface of the personal digital assistant 510 where a display unit 420 is provided. The disposition of the film unit 64 is not limited to that illustrated and may be modified appropriately.

Because the microphone 410 includes the pressure sensor 310, etc., high sensitivity with respect to frequencies in a wide band is possible.

Although the case where the microphone 410 is embedded in the personal digital assistant 510 is shown, this is not limited thereto. The microphone 410 also may be embedded in, for example, an IC recorder, a pin microphone, etc.

Eighth Embodiment

Figure 28A:
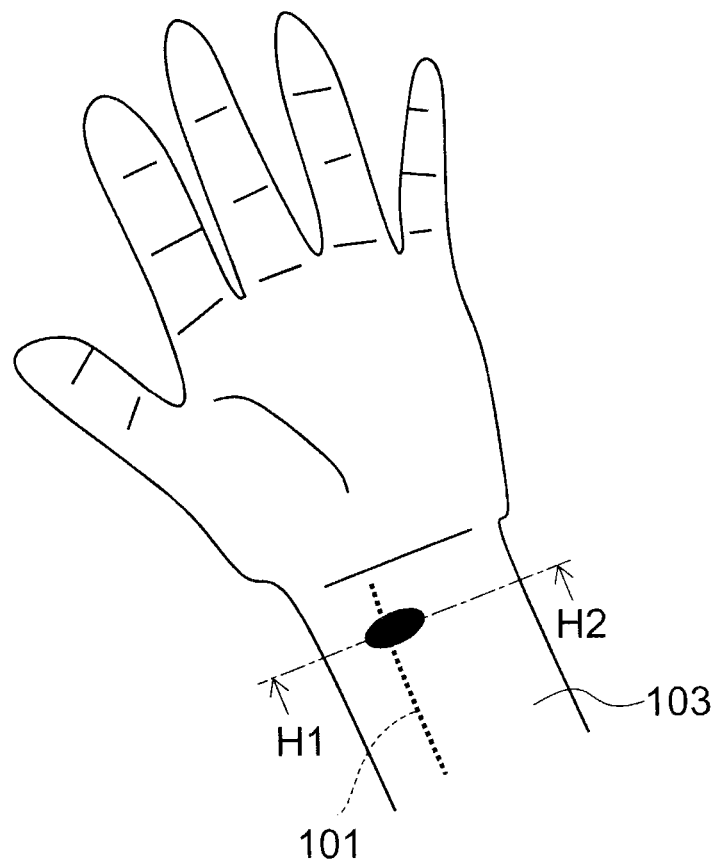
FIGS. 28A and 28B are schematic views showing a blood pressure sensor 330 according to an eighth embodiment.
Figure 28B:
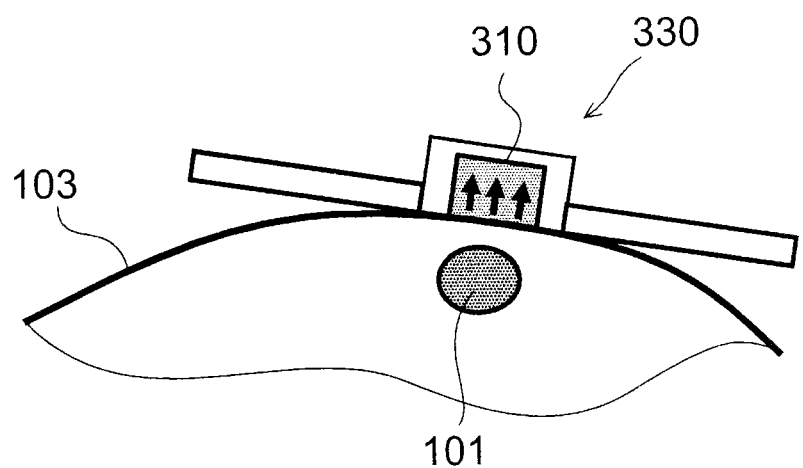

FIGS. 28A and 28B are schematic views showing a blood pressure sensor 330 according to an eighth embodiment.

FIG. 28A is a schematic plan view showing skin on the arterial vessel of a human.

FIG. 28B is a cross-sectional view along line H1-H2 of FIG. 28A.

The blood pressure sensor 330 according to the embodiment includes any pressure sensor (e.g., the pressure sensors 310, 320, 340, or 341) according to the embodiments described above or a pressure sensor according to a modification of these pressure sensors. FIG. 28B shows the case where the blood pressure sensor 330 includes the pressure sensor 310 as an example.

Because the blood pressure sensor 330 includes the pressure sensor 310, etc., a compact and highly-sensitive blood pressure sensor 330 is possible.

Therefore, as shown in FIG. 28B, the portion of the blood pressure sensor 330 where the pressure sensor 310, etc., are provided can be pressed easily onto skin 103 on an arterial vessel 101. As a result, it is possible to perform a continuous and high-precision blood pressure measurement.

Ninth Embodiment

Figure 29:
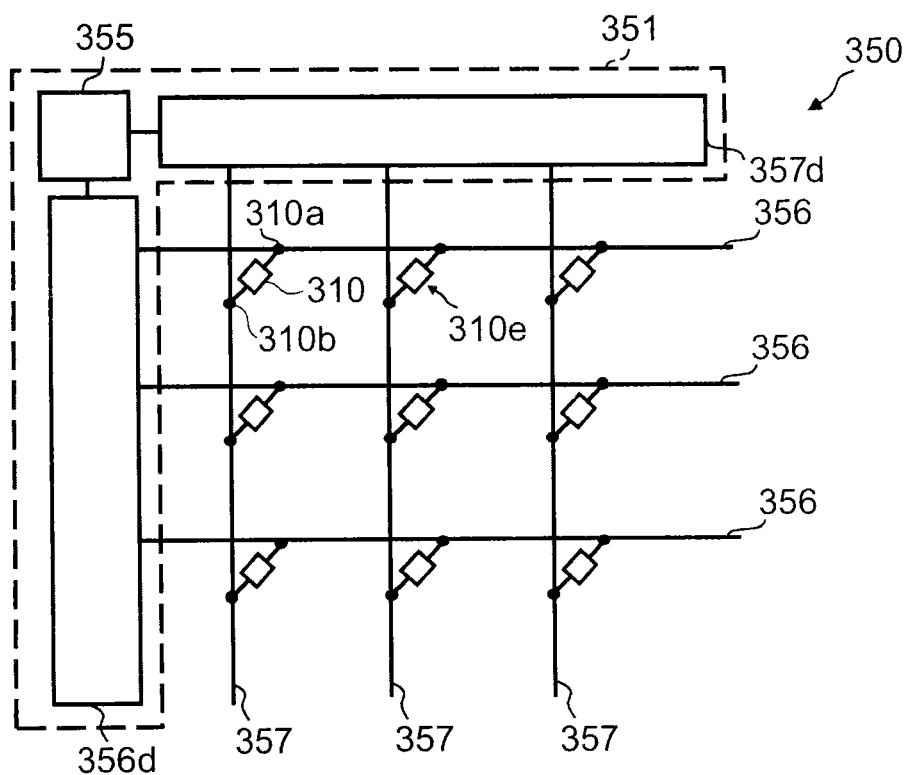
FIG. 29 is a schematic view showing a touch panel 350 according to a ninth embodiment.

FIG. 29 is a schematic view showing a touch panel 350 according to a ninth embodiment. The touch panel 350 according to the embodiment includes any pressure sensor (e.g., the pressure sensors 310, 320, 340, or 341) according to the embodiments described above or a pressure sensor according to a modification of these pressure sensors. FIG. 29 shows the case where the touch panel 350 includes the pressure sensor 310 as an example.

As shown in FIG. 29, multiple first interconnects 356, multiple second interconnects 357, multiple pressure sensors 310, and a control unit 351 are provided in the touch panel 350.

It is sufficient for the pressure sensors 310 to be provided in the interior of the display and/or outside the display of the touch panel 350.

The multiple first interconnects 356 are arranged along a first direction. Each of the multiple first interconnects 356 extends along a second direction that intersects the first direction.

The multiple second interconnects 357 are arranged along a third direction that intersects the first direction. Each of the multiple second interconnects 357 extends along a fourth direction that intersects the third direction.

The first direction and the fourth direction may be the same direction. The second direction and the third direction may be the same direction.

The multiple pressure sensors 310 are provided respectively at the intersections between the multiple first interconnects 356 and the multiple second interconnects 357.

One pressure sensor 310 is used as one sensing component 310e for sensing. Herein, the intersections include the regions around the positions where the first interconnects 356 and the second interconnects 357 intersect.

The interconnects 57 of the multiple pressure sensors 310 are electrically connected to the multiple first interconnects 356 via connection units 310a. The interconnects 58 of the multiple pressure sensors 310 are electrically connected to the multiple second interconnects 357 via connection units 310b.

The control unit 351 is electrically connected to the multiple first interconnects 356 and the multiple second interconnects 357.

For example, the control unit 351 includes a first interconnect circuit 356d that is electrically connected to the multiple first interconnects 356, a second interconnect circuit 357d that is electrically connected to the multiple second interconnects 357, and a control circuit 355 that is electrically connected to the first interconnect circuit 356d and the second interconnect circuit 357d.

When an external pressure is applied to the film unit 64 of the pressure sensor 310, that is, when the sensing component 310e is pressed, a sense signal is sent to the control unit 351; and prescribed processing is performed.

Because the touch panel 350 includes the pressure sensors 310, etc., a compact and highly-sensitive touch panel 350 is possible.

Application examples of the pressure sensors according to the embodiments are not limited to those illustrated. For example, the pressure sensors according to the embodiments may be used in various devices including pressure sensors such as atmospheric pressure sensors, air pressure sensors of tires, etc.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions. Moreover, above-mentioned embodiments can be combined mutually and can be carried out.

What is claimed is:

1. A pressure sensor, comprising:
    a base unit;
    a film unit provided in the base unit, the film unit being flexible; and
    a plurality of sensing elements provided on the film unit radially with respect to a centroid of the film unit, the plurality of sensing elements having a first side and a second side intersecting the first side,
    each of the plurality of sensing elements including a first magnetic layer, a second magnetic layer provided on the film unit, and an intermediate layer provided between the first magnetic layer and the second magnetic layer, the first magnetic layer and the second magnetic layer being free magnetic layers,
    each of the plurality of sensing elements having a shape anisotropy characterized by a length of the first side being longer than a length of the second side,
    the plurality of sensing elements being provided at lines having radial configurations extending from the centroid to have a prescribed angle between the first side and the line.

2. The sensor according to claim 1, wherein each of the sensing elements is provided to cause the first side to be orthogonal to a line extending radially from the centroid of the film surface.

3. The sensor according to claim 1, wherein each of the sensing elements is provided to cause the first side to be parallel to a line extending radially from the centroid of the film surface.

4. The sensor according to claim 1, wherein each of the sensing elements is provided at a line extending radially from the centroid of the film surface to have an angle of substantially 45 degrees between the first side and the line.

5. The sensor according to claim 1, wherein each of the sensing elements is provided to cause at least one selected from a magnetization direction of the first magnetic layer and a magnetization direction of the second magnetic layer to be orthogonal to a line extending radially from the centroid of the film surface.

6. The sensor according to claim 1, wherein a magnetization direction of the first magnetic layer is different from a magnetization direction of the second magnetic layer.

7. The sensor according to claim 1, wherein at least two of the plurality of sensing elements are electrically connected in series.

8. The sensor according to claim 7, wherein a voltage not less than 1 V and not more than 10 V is applied between terminals of the sensing elements electrically connected in series.

9. The sensor according to claim 7, wherein the number of the sensing elements electrically connected in series is not less than 6 and not more than 200.

10. The sensor according to claim 1, wherein the dimension of the first side is not less than 0.2 μm and not more than 60 μm.

11. The sensor according to claim 1, wherein a planar configuration of each of the sensing elements is a quadrilateral.

12. A pressure sensor, comprising:
    a base unit;
    a hollow portion provided in the base unit;
    a film unit provided in the base unit, the film unit being flexible; and
    a plurality of sensing elements provided on the film unit, the plurality of sensing elements having a first side and a second side intersecting the first side,
    each of the plurality of sensing elements including a first magnetic layer, a second magnetic layer provided on the film unit, and an intermediate layer provided between the first magnetic layer and the second magnetic layer, the first magnetic layer and the second magnetic layer being free magnetic layers,
    each of the plurality of sensing elements having a shape anisotropy characterized by a length of the first side being longer than a length of the second side,
    each of the plurality of sensing elements being provided along a circumferential edge of an opening of the hollow portion.

13. The sensor according to claim 12, wherein each of the sensing elements is provided to cause at least one selected from a magnetization direction of the first magnetic layer and a magnetization direction of the second magnetic layer to be orthogonal to a line extending radially from the centroid of the film surface.

14. The sensor according to claim 12, wherein a magnetization direction of the first magnetic layer is different from a magnetization direction of the second magnetic layer.

15. The sensor according to claim 12, wherein at least two of the plurality of sensing elements are electrically connected in series.

16. The sensor according to claim 15, wherein a voltage not less than 1 V and not more than 10 V is applied between terminals of the sensing elements electrically connected in series.

17. The sensor according to claim 12, wherein the dimension of the first side is not less than 0.2 μm and not more than 60 μm.

18. A microphone comprising the sensor according to claim 1.

19. A blood pressure sensor comprising the sensor according to claim 1.

20. A touch panel comprising the sensor according to claim 1.

* * * * *